United States Patent
Bruszewski

(10) Patent No.: US 8,337,546 B2
(45) Date of Patent: Dec. 25, 2012

(54) MOBILE EXTERNAL COUPLING FOR BRANCH VESSEL CONNECTION

(75) Inventor: Walter Bruszewski, Windsor, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 273 days.

(21) Appl. No.: 12/770,566

(22) Filed: Apr. 29, 2010

(65) Prior Publication Data

US 2011/0270380 A1    Nov. 3, 2011

(51) Int. Cl.
*A61F 2/06* (2006.01)
(52) U.S. Cl. .................. 623/1.35; 623/1.15; 623/1.13
(58) Field of Classification Search .............. 623/1.15, 623/1.13, 1.35
See application file for complete search history.

(56) References Cited

U.S. PATENT DOCUMENTS

| | | | |
|---|---|---|---|
| 3,692,618 A | 9/1972 | Dorschner et al. |
| 3,802,817 A | 4/1974 | Matsuki et al. |
| 4,340,563 A | 7/1982 | Appel et al. |
| 5,387,235 A | 2/1995 | Chuter |
| 5,456,713 A | 10/1995 | Chuter |
| 5,693,084 A | 12/1997 | Chuter |
| 5,709,713 A | 1/1998 | Evans et al. |
| 5,720,776 A | 2/1998 | Chuter et al. |
| 5,755,772 A | 5/1998 | Evans et al. |
| 5,800,514 A | 9/1998 | Nunez et al. |
| 6,248,067 B1 | 6/2001 | Causey, III et al. |
| 6,465,073 B1 | 10/2002 | Morman et al. |
| 6,565,597 B1 | 5/2003 | Fearnot et al. |
| 6,994,724 B2 | 2/2006 | Schmitt |
| 7,189,257 B2 | 3/2007 | Schmitt et al. |
| 7,264,632 B2 | 9/2007 | Wright et al. |
| 2003/0199967 A1 | 10/2003 | Hartley |
| 2005/0143806 A1 | 6/2005 | Phillips |
| 2006/0229561 A1 | 10/2006 | Huszar |
| 2006/0276883 A1 | 12/2006 | Greenberg et al. |
| 2007/0135904 A1 | 6/2007 | Eidenschink |
| 2007/0244542 A1 | 10/2007 | Greenan et al. |
| 2008/0114442 A1 | 5/2008 | Mitchell et al. |
| 2008/0262590 A1 | 10/2008 | Murray |
| 2009/0264991 A1* | 10/2009 | Paul et al. ................. 623/1.35 |

(Continued)

FOREIGN PATENT DOCUMENTS

EP    0556749    2/1993

(Continued)

OTHER PUBLICATIONS

U.S. Appl. No. 12/425,616, filed Apr. 2009, Bruszewski et al.

(Continued)

*Primary Examiner* — Thomas J Sweet
*Assistant Examiner* — Jason-Dennis Stewart

(57) ABSTRACT

An endovascular prosthesis includes a tubular body and a mobile external coupling. The tubular body includes a graft material and stents coupled thereto which forms a lumen therethrough. The mobile external coupling extends outwardly from the tubular body. The mobile external coupling includes a graft material and is generally frustoconically shaped. The mobile external coupling includes a base coupled to the tubular body, a top spaced from the tubular body, and a coupling lumen disposed between the base and the top, wherein the coupling lumen is in flow communication with the body lumen. A coupling deployment device is coupled to the coupling graft material to provide an extension force to extend the mobile external coupling from a collapsed configuration against the tubular body to an extended position wherein the mobile external coupling extends from the tubular body.

35 Claims, 19 Drawing Sheets

U.S. PATENT DOCUMENTS

2009/0276027 A1  11/2009  Glynn
2010/0063578 A1*  3/2010  Ren et al. .................... 623/1.15

FOREIGN PATENT DOCUMENTS

| EP | 1201212 | 5/2002 |
|---|---|---|
| WO | WO93/16669 | 9/1993 |
| WO | WO2005/034809 | 4/2005 |
| WO | WO2005/037160 | 4/2005 |
| WO | WO2006/113501 | 10/2006 |

OTHER PUBLICATIONS

U.S. Appl. No. 12/425,628, filed Apr. 2009, Bruszewski et al.

* cited by examiner

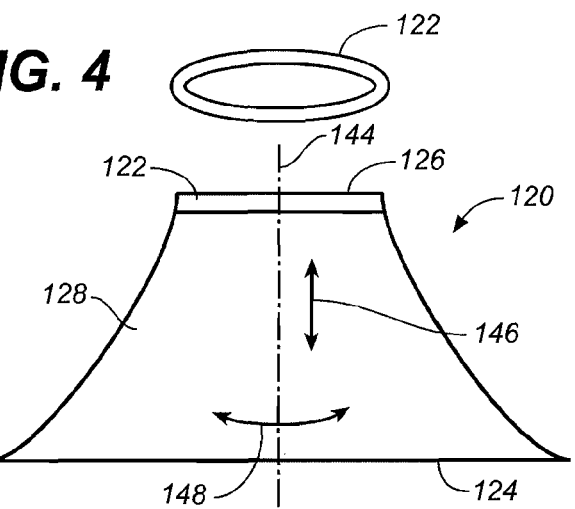
FIG. 4
FIG. 3
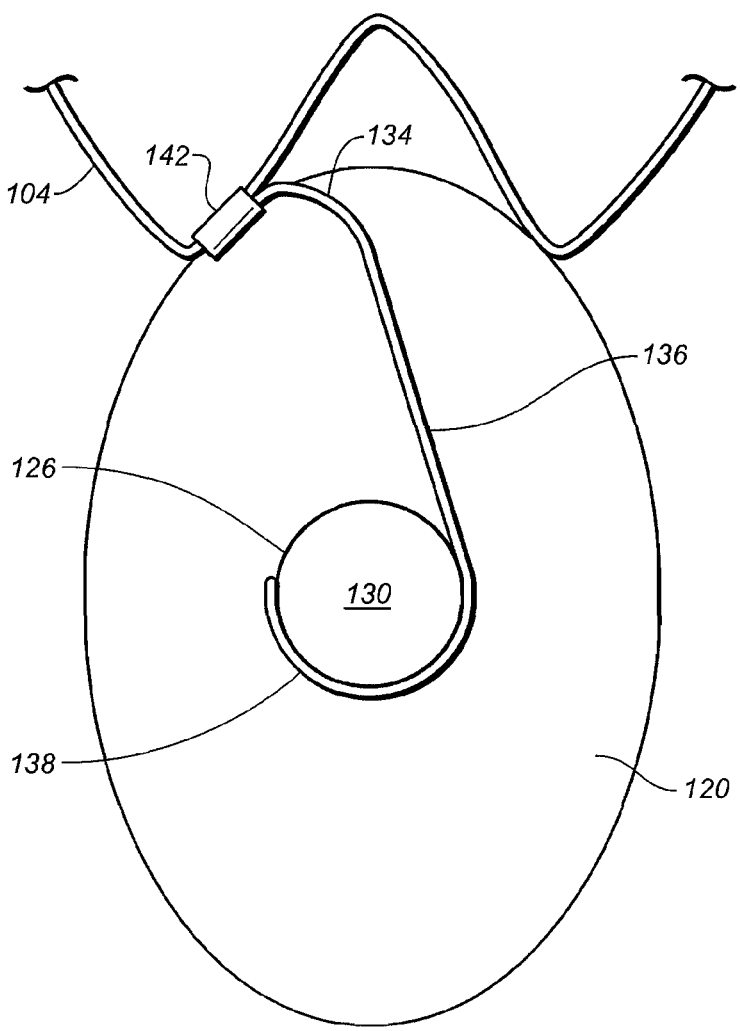
FIG. 5

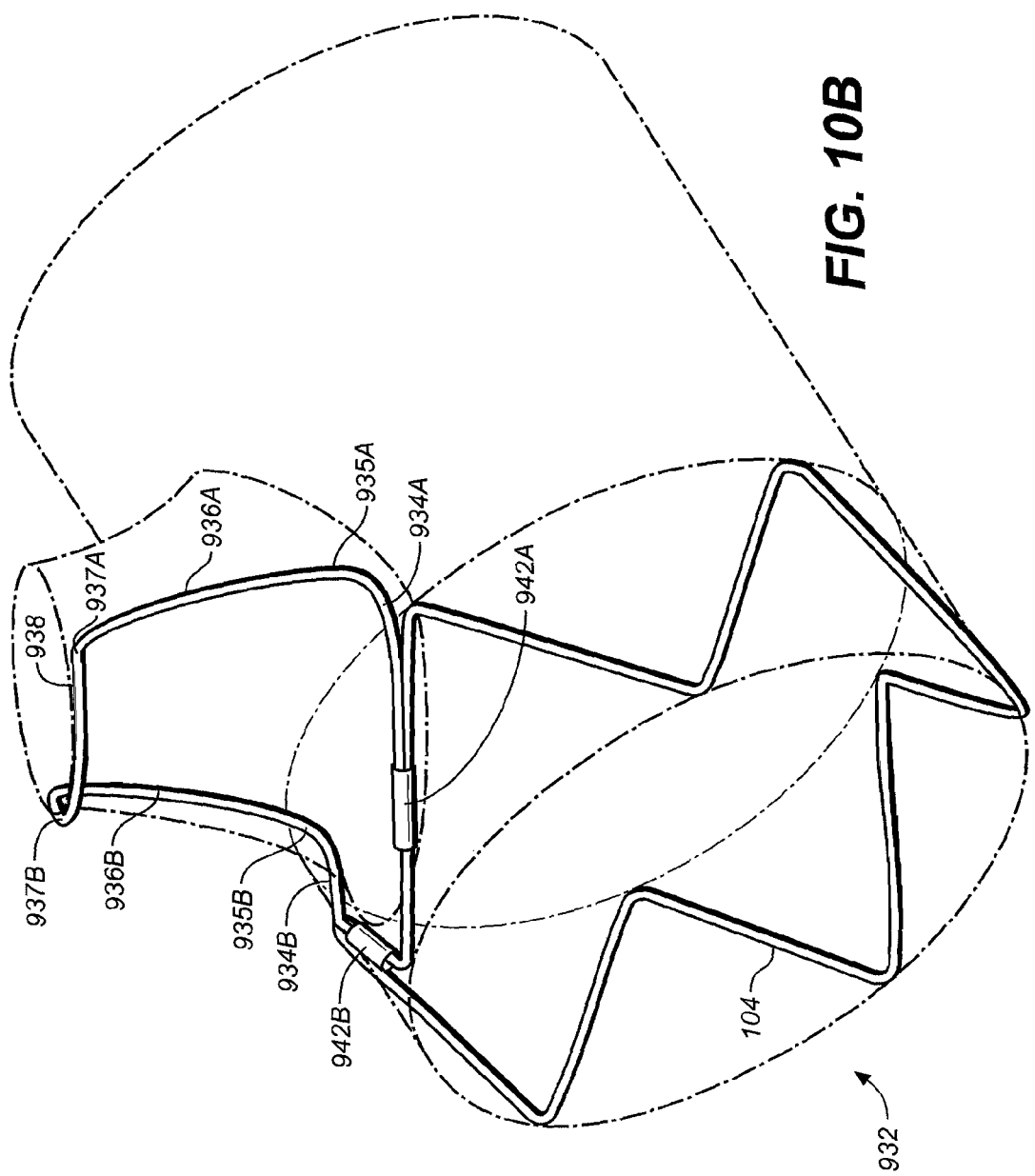

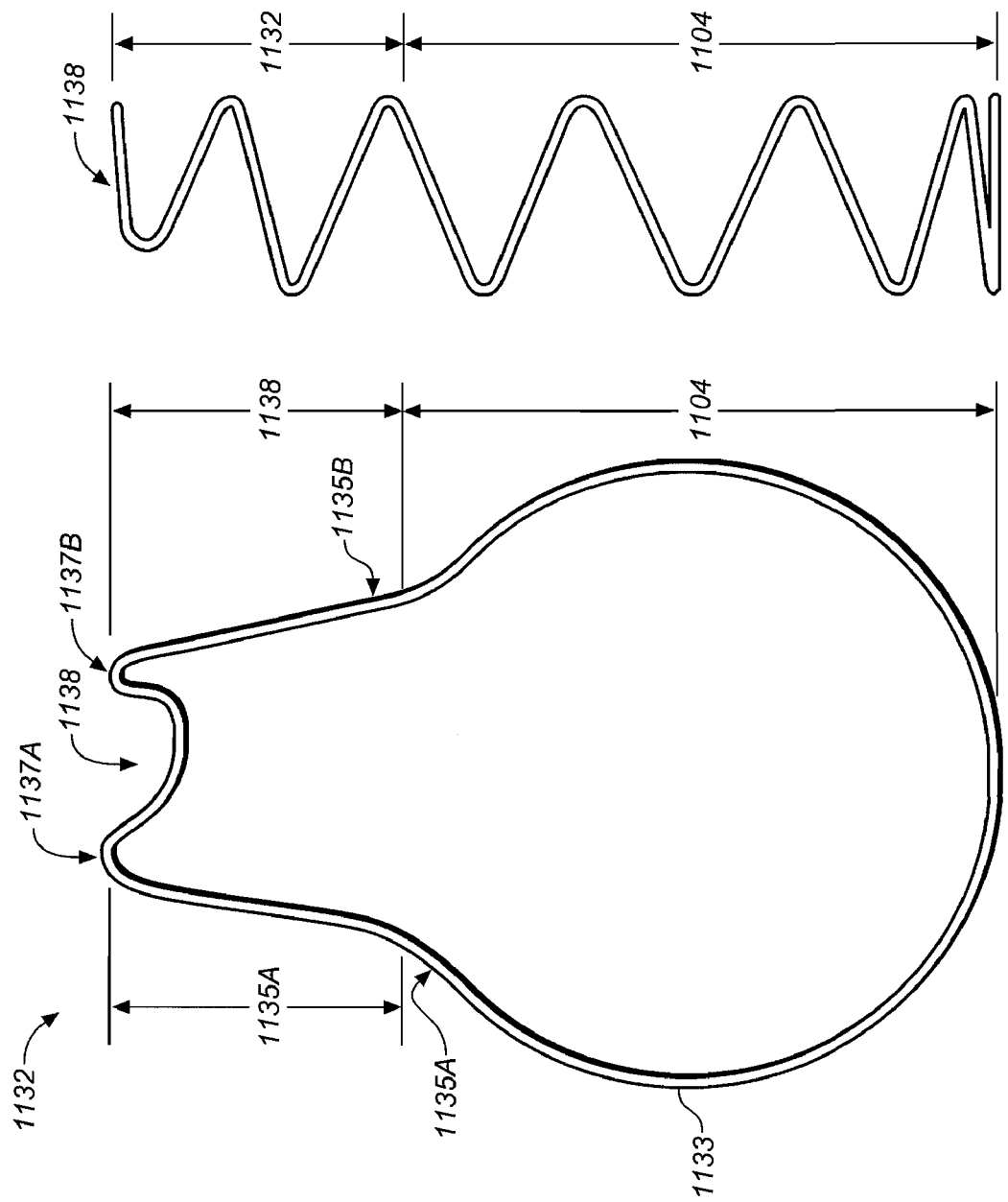

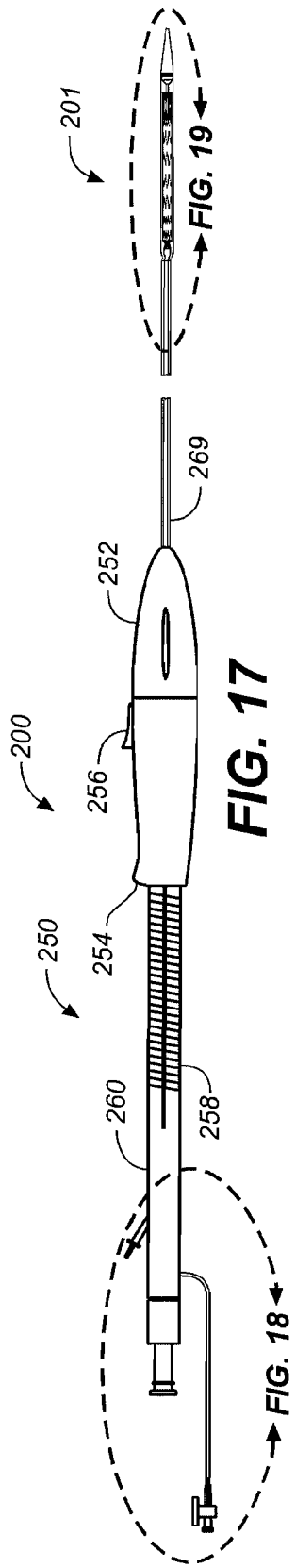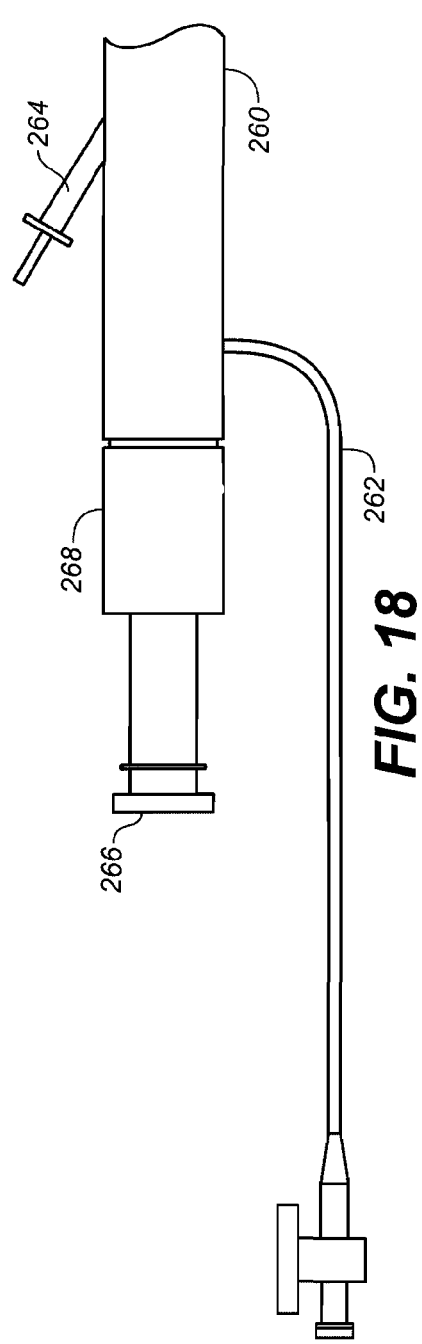

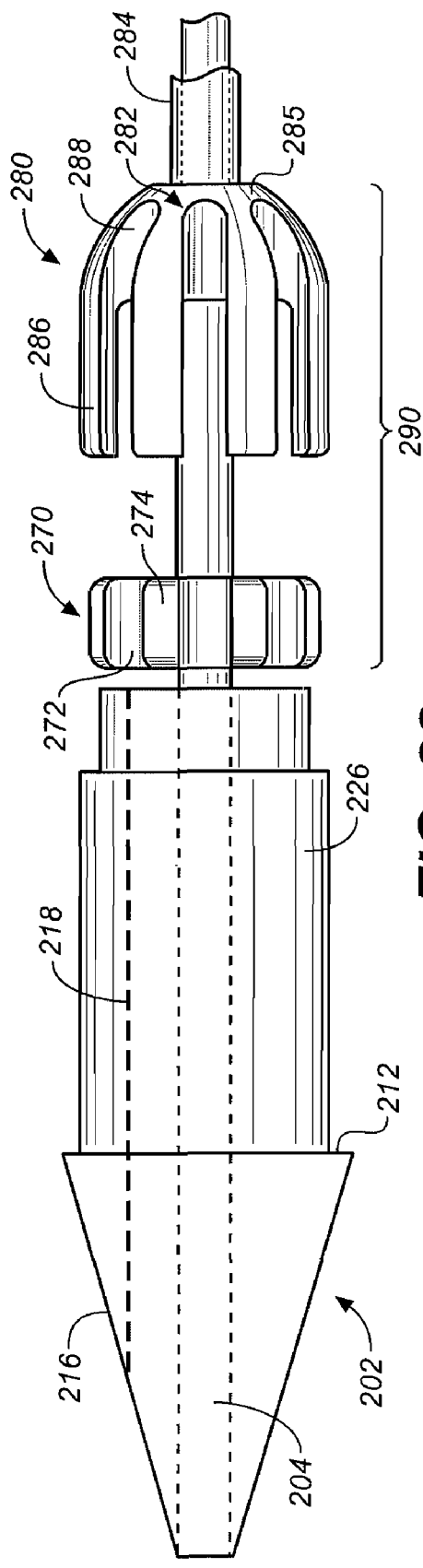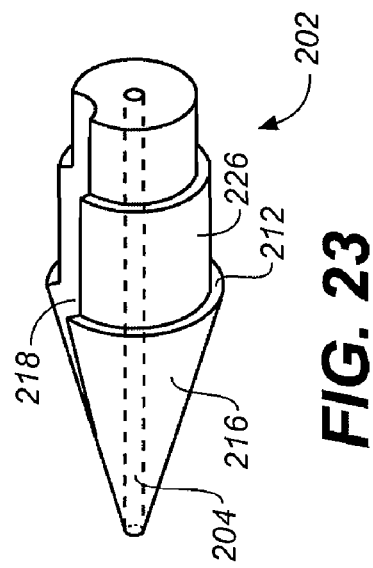
FIG. 22
FIG. 23

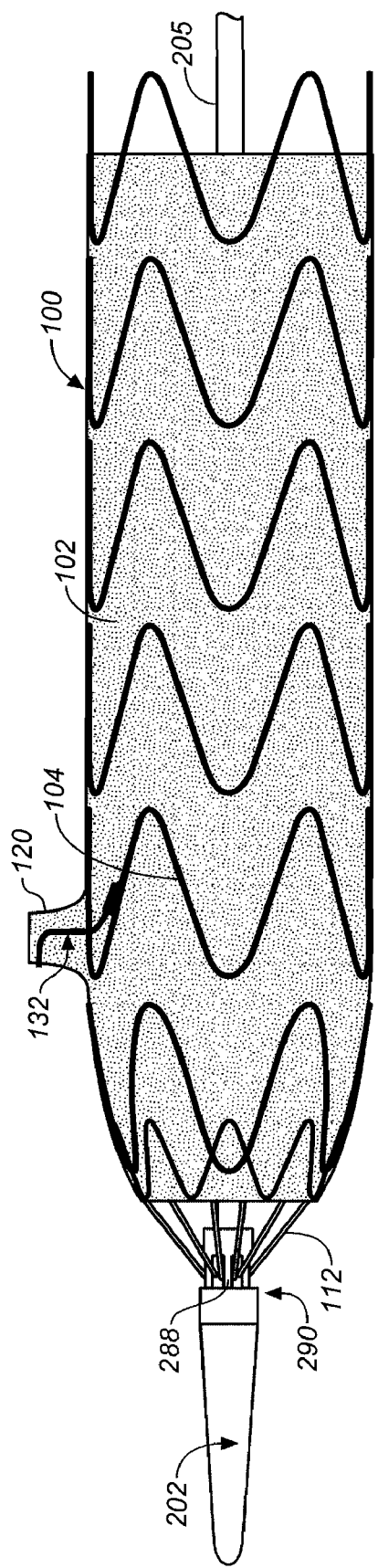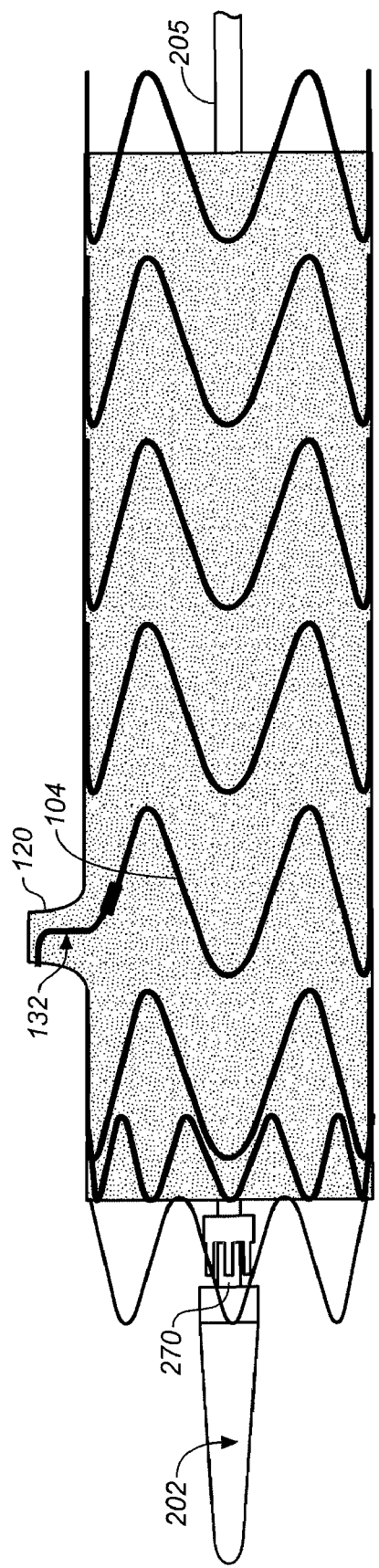

MOBILE EXTERNAL COUPLING FOR BRANCH VESSEL CONNECTION

FIELD OF THE INVENTION

This invention relates generally to endoluminal medical devices and procedures, and more particularly to an endoluminal prosthesis or graft having a mobile external coupling for connecting a main graft to a branch vessel graft.

BACKGROUND

Aneurysms and/or dissections may occur in blood vessels, and most typically occur in the aorta and peripheral arteries. Depending on the region of the aorta involved, the aneurysm may extend into areas having vessel bifurcations or segments of the aorta from which smaller "branch" arteries extend. Various types of aortic aneurysms may be classified on the basis of the region of aneurysmal involvement. For example, thoracic aortic aneurysms include aneurysms present in the ascending thoracic aorta, the aortic arch, and branch arteries that emanate therefrom, such as subclavian arteries, and also include aneurysms present in the descending thoracic aorta and branch arteries that emanate therefrom, such as thoracic intercostal arteries and/or the suprarenal abdominal aorta and branch arteries that emanate therefrom, such as renal, superior mesenteric, celiac and/or intercostal arteries. Abdominal aortic aneurysms include aneurysms present in the aorta below the diaphragm, e.g., pararenal aorta and the branch arteries that emanate therefrom, such as the renal arteries.

The thoracic aorta has numerous arterial branches. The arch of the aorta has three major branches extending therefrom, all of which arise from the convex upper surface of the arch and ascend through the superior thoracic aperture to the root of the neck. The brachiocephalic artery originates anterior to the trachea. The brachiocephalic artery divides into two branches, the right subclavian artery (which supplies blood to the right arm) and the right common carotid artery (which supplies blood to the right side of the head and neck). The left common carotid artery arises from the arch of the aorta just to the left of the origin of the brachiocephalic artery. The left common carotid artery supplies blood to the left side of the head and neck. The third branch arising from the aortic arch, the left subclavian artery, originates behind and just to the left of the origin of the left common carotid artery and supplies blood to the left arm.

For patients with thoracic aneurysms of the aortic arch, surgery to replace the aorta may be performed where the aorta is replaced with a fabric substitute in an operation that uses a heart-lung machine. In such a case, the aneurysmal portion of the aorta is removed or opened and a substitute lumen is sewn across the aneurysmal portion to span it. Such surgery is highly invasive, requires an extended recovery period and, therefore, cannot be performed on individuals in fragile health or with other contraindicative factors.

Alternatively, the aneurysmal region of the aorta can be bypassed by use of an endoluminally delivered tubular exclusion device, e.g., by a stent-graft placed inside the vessel spanning the aneurysmal portion of the vessel, to seal off the aneurysmal portion from further exposure to blood flowing through the aorta. A stent-graft can be implanted without a chest incision, using specialized catheters that are introduced through arteries, usually through incisions in the groin region of the patient. The use of stent-grafts to internally bypass, within the aorta or flow lumen, the aneurysmal site, is also not without challenges. In particular, where a stent-graft is used in a thoracic location, care must be taken so that critical branch arteries are not covered or occluded by the stent-graft yet the stent-graft must seal against the aorta wall and provide a flow conduit for blood to flow past the aneurysmal site. Where the aneurysm is located immediately adjacent to the branch arteries, there is a need to deploy the stent-graft at a location which partially or fully extends across the location of the origin of the branch arteries from the aorta to ensure sealing of the stent-graft to the artery wall.

To accommodate side branches, main vessel stent-grafts having a fenestration or opening in a side wall thereof may be utilized. The main vessel stent graft is positioned to align its fenestration with the ostium of the branch vessel. In use, a proximal end of the stent-graft, having one or more side openings, is prepositioned and securely anchored in place so that its fenestrations or openings are oriented and deployed in the main vessel to avoid blocking or restricting blood flow into the side branches. Fenestrations by themselves do not form or include discrete conduit(s) through which blood can be channeled into the adjacent side branch artery. As a result, blood leakage is prone to occur into the space between the outer surface of the main aortic stent graft and the surrounding aortic wall between the edge of the graft material surrounding the fenestrations and the adjacent vessel wall. Similar blood leakage can result from post-implantation migration or movement of the stent-graft causing misalignment between the fenestration(s) and the branch artery(ies), which may also result in impaired flow into the branch artery(ies).

In some cases, the main vessel stent graft is supplemented by another stent-graft, often referred to as a branch stent-graft. The branch graft is deployed through the fenestration into the branch vessel to provide a conduit for blood flow into the branch vessel. The branch stent-graft is preferably sealingly connected to the main graft in situ to prevent undesired leakage between it and the main stent graft. This connection between the branch graft and main graft may be difficult to create effectively in situ and is a site for potential leakage.

In some instances, branch graft extensions (stent-grafts) are incorporated into the main stent-graft. Such branch graft extensions are folded or collapsed against the main stent-graft for delivery and require complicated procedures, requiring multiple sleeves and guide wires, to direct the branch extension into the branch vessel and subsequently expand. Further, in some instances, such branch stent-grafts tend to return to their folded or collapsed configuration, and thus do not provide an unobstructed flow path to the branch vessel.

Thus, there remains a need in the art for improvements for directing flow from a main vessel, such as the aorta, into corresponding branch vessels, such as branch vessels of the aortic arch.

SUMMARY OF THE INVENTION

Embodiments hereof relate to an endovascular prosthesis including a tubular body and a mobile external coupling. The tubular body includes graft material and stents coupled thereto, to hold open a lumen therethrough. The mobile external coupling extends outwardly from the tubular body. The mobile external coupling includes graft material and is generally frustoconically shaped. The mobile external coupling includes a base coupled to the tubular body, a top spaced from the tubular body, and a coupling lumen disposed between the base and the top, wherein the coupling lumen is in flow communication with the body lumen. A coupling deployment device is coupled to the mobile external coupling. The coupling deployment device is a shape memory wire that is coupled to one of the stents coupled to tubular body graft material. The coupling deployment device provides as outward force due to stored energy when the mobile external coupling is a released at a treatment site. In an embodiment, the coupling deployment device includes a base segment connected to a circumferential stent in a cantilever fashion such that the base segment is generally transverse to a longitudinal axis of the mobile external coupling. The coupling deployment device further includes a spring arm running generally longitudinally along the mobile external coupling and an apical segment running generally circumferentially around the top of the mobile external coupling. A first hinge connects the base segment to the spring arm and a second hinge connects the spring arm and the apical segment. The spring arms provide a sufficient outward force to the mobile external coupling to be is released at the treatment site, while providing sufficient flexibility to properly locate the mobile external coupling at a branch vessel.

In another embodiment, the coupling deployment device has its own support or base stent disposed around the body of the stent-graft adjacent the mobile external coupling. The base stent extends around a significant portion of the circumference of the body, but does not extend completely around the body of the stent-graft. Rather, the base stent includes an extension or integral coupling deployment device that is coupled to mobile external coupling to extend the mobile external coupling away from the body and into the ostium of the target branch vessel during deployment to ensure that the mobile external coupling fully extends into the ostium. The coupling deployment device includes first and second spring arms and a semicircular apical segment disposed at the top of the mobile external coupling. A first hinge or turn is integrally formed between the first spring arm and the apical segment, and a second hinge or turn is integrally formed between second spring arm and the apical segment. The spring arms are formed into a zig-zag or sinusoidal configuration and are shape set such that when the mobile external coupling is released its delivery device, the stored energy in the spring arms provides a force to extend or "pop-out" the mobile external coupling from the body.

BRIEF DESCRIPTION OF DRAWINGS

The foregoing and other features and advantages of embodiments according to the invention will be apparent from the following description as illustrated in the accompanying drawings. The accompanying drawings, which are incorporated herein and form a part of the specification, further serve to explain the principles of the embodiments and enable a person skilled in the pertinent art to make and use the described embodiments herein. The drawings are not to scale.

FIG. 3 is a schematic illustration of the mobile external coupling of the stent-graft of FIG. 1, wherein the coupling deployment device is removed for clarity.

FIG. 4 is a schematic illustration of a sealing ring disposed at the top of the mobile external coupling of FIG. 3.

FIG. 5 is a schematic top view of the mobile external coupling and the coupling deployment device of FIG. 1.

FIGS. 10A and 10B are images of the coupling deployment device of FIG. 9 attached to a circumferential stent.

FIG. 13 is an end view image of a circumferential stent having the integral coupling deployment device of FIG. 11.

FIG. 14 is a side view image of a circumferential stent having the integral coupling deployment device of FIG. 11.

FIG. 17 is a schematic illustration of a stent-graft delivery device.

FIG. 18 is a schematic illustration of a proximal portion of the stent-graft delivery device of FIG. 17.

FIG. 22 is a schematic illustration of a stent capture assembly of the delivery system of FIG. 17.

FIG. 23 is a schematic illustration of the tip of the delivery system of FIG. 17.

FIGS. 24-27 are various schematic illustrations of progressive steps of deploying the stent-graft from the delivery system of FIG. 17.

DETAILED DESCRIPTION

Figure 1:
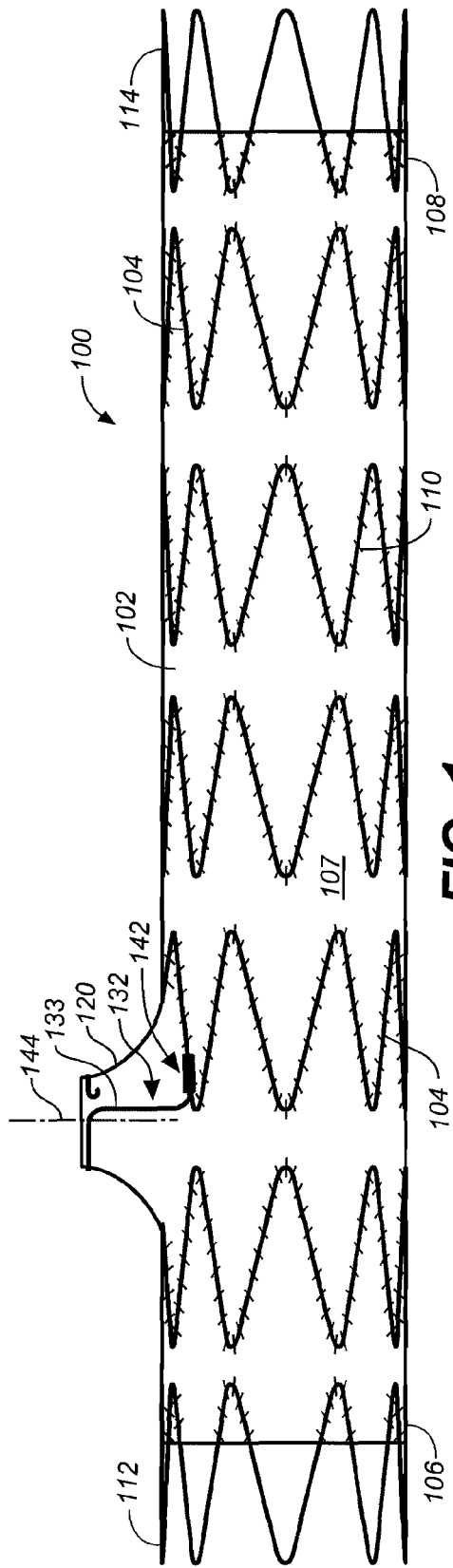
FIG. 1 is a schematic side view of an embodiment of an endoluminal stent-graft.

Specific embodiments are now described with reference to the figures, wherein like reference numbers indicate identical or functionally similar elements. Unless otherwise indicated, for the delivery system the terms "distal" and "proximal" are used in the following description with respect to a position or direction relative to the treating clinician. "Distal" and "distally" are positions distant from or in a direction away from the clinician, and "proximal" and "proximally" are positions near or in a direction toward the clinician. For the stent graft device proximal is the portion nearer the heart by way of blood flow path while distal is the portion of the stent graft further from the heart by way of blood flow path.

With reference to FIGS. 1-7, a stent-graft 100 is configured for placement in a vessel such as the aorta. Stent-graft 100 includes graft material 102 coupled to circumferential stents 104. Graft material 102 may be coupled to circumferential stents 104 using stitching 110 or other means known to those of skill in the art. In the embodiment shown in FIGS. 1-3 circumferential stents 104 are coupled to an outside surface of graft material 102. However, circumferential stents 104 may alternatively be coupled to an inside surface of graft material 102. Graft material 102 may be any suitable graft material, for example and not limited to, woven polyester, DACRON material, expanded polytetrafluoroethylene, polyurethane, silicone, or other suitable materials. Circumferential stents 104 may be any conventional stent material or configuration. As shown, circumferential stents 104 are preferably made from a shape memory material, such as thermally treated stainless steel or nickel-titanium alloy (nitinol), and are formed into a zig-zag configuration. Stent-graft 100 includes a proximal end 106, a distal end 108, and a body 107 therebetween. Proximal stent 112 and distal stent 114 may extend outside of the graft material 102, as shown, and may also be generally described as anchor, bare, or crown stents in the art. Body 107 has a lumen 116 therethrough. Stent-graft 100 further includes a mobile external coupling 120, described in detail below. Except for the mobile external coupling 120, stent graft-100 may be similar to the Medtronic, Inc.'s VALIANT® thoracic stent-graft, or other known stent-grafts.

Mobile external coupling 120 is disposed on an outside surface of stent-graft 100 corresponding to an opening in graft material 102. Mobile external coupling 120 is generally frustoconically shaped. Mobile external coupling 120 includes graft material 128 having a base 124 and a top 126. Graft material 128 is preferably the same type of graft material as graft material 102 of the body 107 and is preferably a continuation of graft material 102, although graft material 128 can be a separate piece of graft material attached to graft material 102. As shown in FIGS. 3 and 4, a wire shaped as a circle or ring 122 may be disposed at top 126, for example by folding graft material 128 over ring 122 and stitching the folded over portion of the graft material 128 to itself. Although mobile external coupling 120 is described as generally frustoconical in shape, base 124 is preferably generally elliptical rather than circular. Base 124 may have, for example and not by way of limitation, a long axis of approximately 20-30 mm and a short axis of approximately 15-20 mm. Further, the height of mobile external coupling 120 may be approximately 10-15 mm. Further, the diameter of the top 126 of mobile external coupling may be approximately 6-9 mm if it is to be used at the junction of the aorta and left common carotid artery or the junction of the aorta and left subclavian artery. If the mobile external coupling 120 is to be used at the junction of the aorta and the brachiocephalic artery, the diameter of the top 126 may be approximately 8-12 mm.

A coupling deployment device 132 is coupled to mobile external coupling 120 for elevating top 126 of mobile external coupling 120 into the ostium of the target branch vessel during deployment and ensuring that mobile external coupling 120 extends fully into the ostium. Coupling deployment device 132 is formed from a tubular structure or wire 133 of a biocompatible resilient material such as nitinol, 316L stainless steel, MP35N spring wire, an acetal copolymer, or a polymeric material having shape memory characteristics. Coupling deployment device 132 may be made from the same material as main body circumferential stents 104 or may be made from different material. For example, circumferential stents 104 may be balloon expandable and coupling deployment device 132 may be self-expanding. Preferably, circumferential stents 104 and coupling deployment device 132 are made from shape memory materials such as nitinol and are self-expanding. In various embodiments, wire 133 may be solid or hollow and have a circular cross-section. In an embodiment, wire 133 has a diameter between 0.008 inch-0.016 inch, whereas circumferential stents 104 are generally about 0.018 inch to 0.021 inch in diameter. In one embodiment, the cross-section of wire 133 may be an oval, square, rectangular, or any other suitable shape. Coupling deployment device 132 is shape set such that a spring arm portion thereof, described in more detail below, extends generally longitudinally along mobile external coupling 120. In a delivery configuration, the mobile external coupling is compressed against body 107 such that coupling deployment device 132 stores energy. When mobile external coupling 120 is released from its delivery configuration, as explained in more detail below, the energy in coupling deployment device 132 is released such that mobile external coupling 120 extends away from body 107.

Mobile external coupling 120 is also sufficiently flexible in directions transverse to its longitudinal axis 144 to allow for significant flexibility in aligning stent-graft 100 with a branch vessel. This mobility is due to the shape of mobile external coupling 120 and can be further improved by utilizing some excess graft material 128 when forming mobile external coupling 120. Thus, if stent-graft 100 is not perfectly aligned with a branch vessel, the top 126 of mobile external coupling 120 can move or shift to cause its top 126 and the excess graft material 128 connected to the top 126 to extend into the branch vessel. Further, due to the energy stored in the shape memory coupling deployment device 132 while in the delivery system, mobile external coupling 120 pops out from body 107 of stent-graft 100 when released from a sleeve (delivery system) during delivery and deployment at a target site. This prevents bunching, kinking, collapse or eversion of the mobile external coupling 120 when released from the delivery system.

Figure 6:
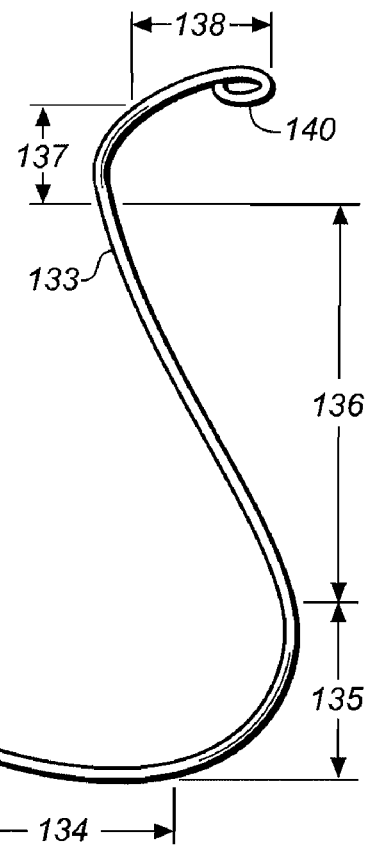
FIG. 6 is an image of the coupling deployment device of FIG. 5.
Figure 7:
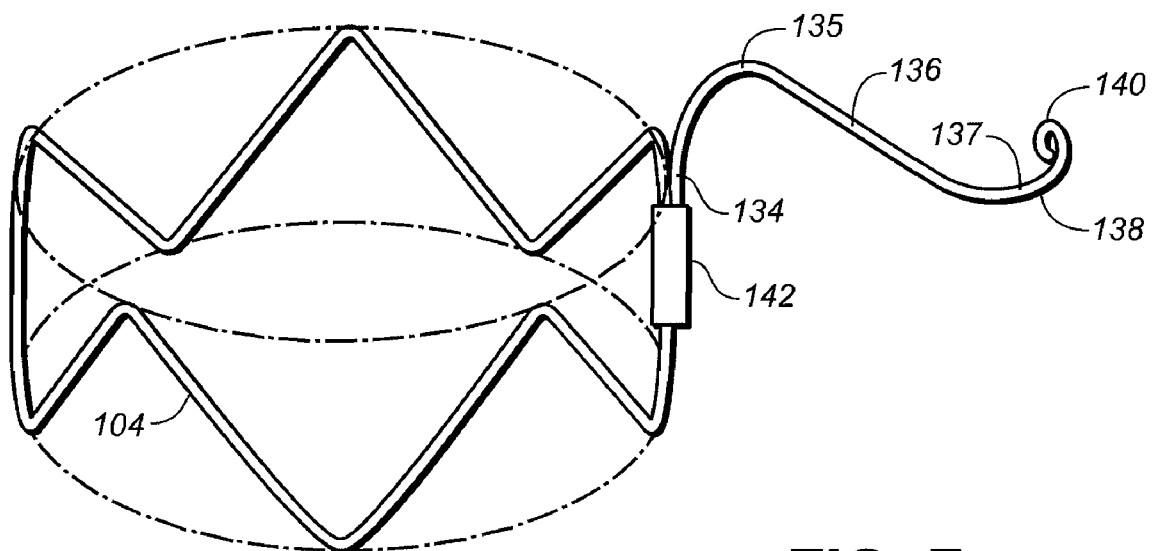
FIG. 7 is an image of the coupling deployment device of FIG. 6 attached to a circumferential stent.

As illustrated in FIGS. 5-7, coupling deployment device, e.g., 132, includes a base segment 134, a spring arm 136, and an apical segment 138. In one embodiment, coupling deployment device 132 is a unitary structure formed out of a single piece of material. A first turn or hinge 135 is integrally formed with and positioned between base segment 134 and spring arm 136, and a second turn or hinge 137 is integrally formed with and positioned between spring arm 136 and apical segment 138. Hinges 135, 137 store energy when couple deployment device 132 is in a compressed configuration for delivery. In another embodiment, the coupling deployment device includes a spring arm that is a separate component that is attached to the base and apical segments by any suitable manner known in the art such as for example welding, including resistance welding, friction welding, laser welding or another form of welding, soldering, using an adhesive, adding a connecting element there between, or by another mechanical method.

Base segment 134 is a relatively short and substantially straight segment that extends generally transverse to a longitudinal axis 144 of mobile external coupling 120, along a direction indicated by arrow 148 of FIG. 3. Base segment 134 is coupled to a circumferential stent 104 of stent-graft 100 in a cantilever fashion via a crimp 142. In one embodiment, crimp 142 may also join the two ends of circumferential stent 104. Since circumferential stents 104 are coupled to an outside surface of graft material 102 in the embodiment shown in FIG. 1, wire 133 of coupling deployment device 132 extends over the outside surfaces of graft material 102 and mobile external coupling 120. However, if circumferential stents 104 are alternatively coupled to an inside surface of graft material 102, wire-like structure 133 of coupling deployment device 132 may extend within the inside surfaces of graft 102 and mobile external coupling 120.

As shown in FIG. 5, spring arm 136 is a substantially straight segment that extends generally longitudinally along mobile external coupling 120, in a direction indicated by arrow 146 of FIG. 3. As used herein with respect to the spring arm or arms of embodiments described herein, the term longitudinally means extending generally in the direction of the length of mobile external coupling 120, or extending generally in the direction of longitudinal axis 144. However, as used herein, the term longitudinally is not restricted to the spring arm 136 running parallel to longitudinal axis 144. Spring arm 136 may be generally parallel to longitudinal axis 144, or may be at an angle up to 45° from longitudinal axis 144, in either direction. First hinge 135 twists and curves to connect generally transverse base segment 134 and spring arm 136. In an embodiment, the angle between generally transverse base segment 134 and spring arm 136 is approximately ninety degrees. Further, although described as a substantially straight segment, spring arm 136 may have alternative configurations that extend generally longitudinally along mobile external coupling 120, such as slightly curved around the conical surface of mobile external coupling 120 or a zig-zag or sinusoidal configuration similar to the spring arms of the embodiment depicted in FIGS. 11-16 described herein.

Figure 2:
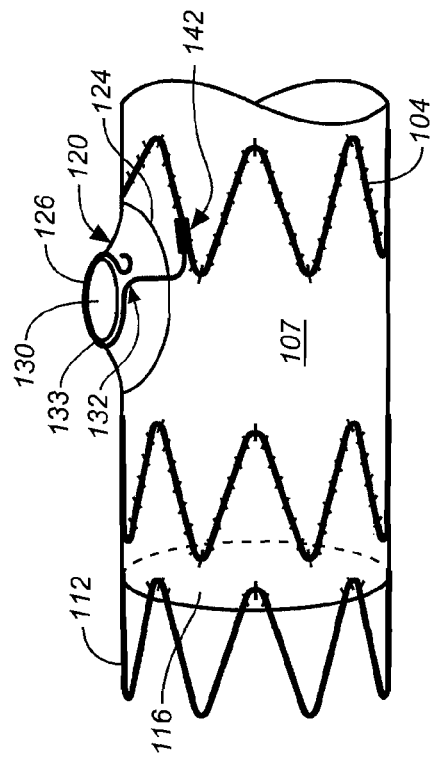
FIG. 2 is a schematic close up illustration of a portion of the stent-graft of FIG. 1.

Apical segment 138 is a curved segment that extends from second hinge 137 to an end 140. As shown in FIG. 2, end 140 of apical segment 138 may include an atraumatic hook or loop to ensure that the end of wire 133 does not cause damage to the patient when mobile external coupling 120 is deployed into the ostium of the target branch vessel. Apical segment 138 extends around top 126 of mobile external coupling 120 in a circumferential manner. Relative to the longitudinal axis 144 of mobile external coupling 120, second hinge 137 twists and curves to connect generally longitudinal spring arm 136 and circumferential apical segment 138. In an embodiment depicted in FIGS. 1-7, apical segment 138 is coupled to ring 122 of mobile external coupling 120 using stitches (e.g., 110) or other similar coupling means. Apical segment 138 may have a generally semi-circular configuration that encircles between 25% and 75% of the circumference of ring 122.

When mobile external coupling 120 and coupling deployment device 132 coupled thereto are loaded in a delivery system, spring arm 136 of coupling deployment device 132 is collapsed along the longitudinal axis of stent-graft 100. Since base segment 134 is crimped to a circumferential stent 104 of stent-graft 100 via a crimp 142, coupling deployment device 132 is anchored to stent-graft 100 and strain ensuing from being collapsed or packed concentrates at first and second hinges 135, 137 of coupling deployment device 132. Energy is accordingly stored within the shape memory material of wire 133 at first hinge 135 and second hinge 137, which results in a high release or deployment force of coupling deployment device 132. In an example, a coupling deployment device with a single spring arm as shown in FIGS. 5-7 was provided on a mobile external coupling having a height of 12 mm and a base of 15×20 mm. The coupling deployment device was made of NiTi wire with diameter of 0.016 inch. The mean maximum deployment or pop-out force was approximately 110 grams-force (1.079 Newtons or 0.243 pounds-force). Further, the force required to move mobile external coupling in a direction transverse to its longitudinal axis 144 (i.e., a side deflection force) was approximately 0.43 pounds-force (195.04 grams-force or 1.91 Newtons). In another example using a NiTi wire with a diameter of 0.018 inch and the single spring arm of FIGS. 5-7 provided on a mobile external coupling as described above, the mean maximum deployment or pop-out force was approximately 280 grams-force (2.746 Newtons or 0.617 pounds-force). Further, the force required to move mobile external coupling in a direction transverse to its longitudinal axis 144 (i.e., a side deflection force) was approximately 0.6 pounds-force (272.16 grams-force or 2.67 Newtons). Those of ordinary skill in the art would appreciate that these are just examples and that the wire size may be varied in order to vary the forces.

Upon release from the delivery system, the stored energy is released such that wire 133 recovers its annealed shape and spring arm 136 lifts or elevates ring 122 located at top 126 of mobile external coupling 120 into the ostium of the target branch vessel to allow for easy antegrade cannulation of the branch vessel. In addition, after wire 133 recovers its annealed shape, coupling deployment device 132 provides a predictable seal with a subsequently delivered branch conduit because it prevents bunching or collapse of the mobile external coupling 120 when released from the delivery system.

Figure 8:
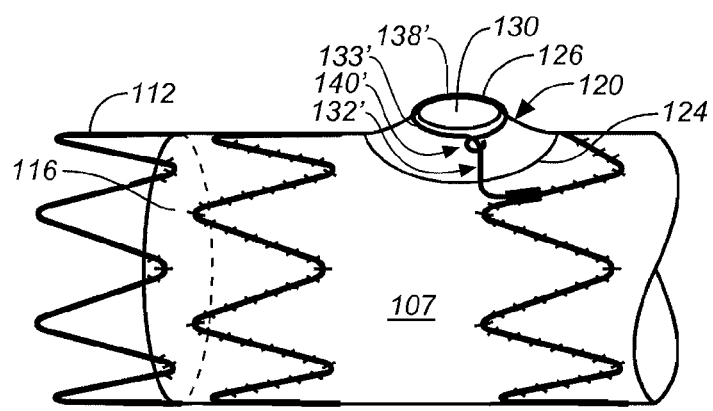
FIG. 8 is a schematic close up illustration of a portion of an endoluminal stent-graft illustrating another embodiment.

In another embodiment hereof, the apical segment of the coupling deployment device may be a complete circle and the ring located at the top of the mobile external coupling may be omitted. Coupling deployment device 132' is similar to coupling deployment device 132 shown in FIG. 1 and the same reference numerals have been used to identify the same parts. As shown in FIG. 8, an annular apical segment 138' of coupling deployment device 132' is coupled to mobile external coupling 120 using stitches (e.g., 110) or other similar coupling means. Apical segment 138' extends around mobile external coupling 120 in a circumferential manner and closes upon itself to form a complete circle at top 126 of mobile external coupling 120. Hooked end 140' may be configured to fasten around wire 133' in order to form annular apical segment 138'. In other embodiments hereof, end 140' may be welded, crimped, or otherwise fastened to wire 133' in order to form a complete circle at the top of the mobile external coupling.

Figure 9:
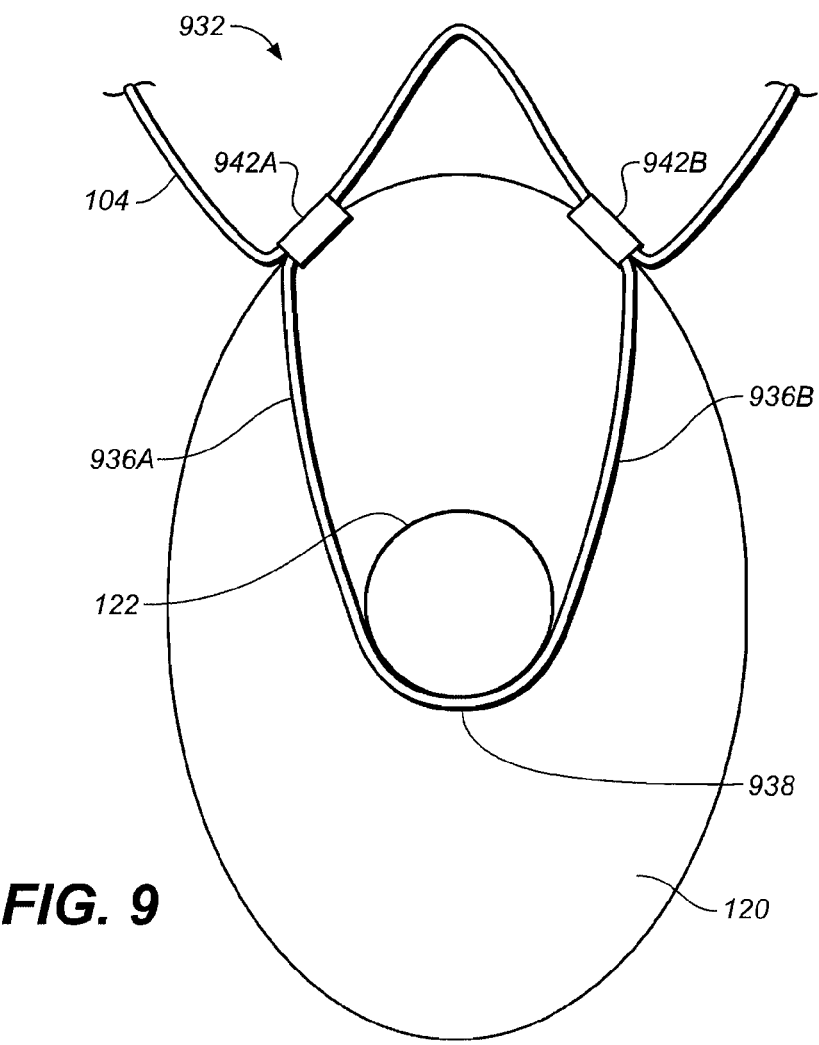
FIG. 9 is a schematic top view of the mobile external coupling and a coupling deployment device illustrating another embodiment.
Figure 10A:
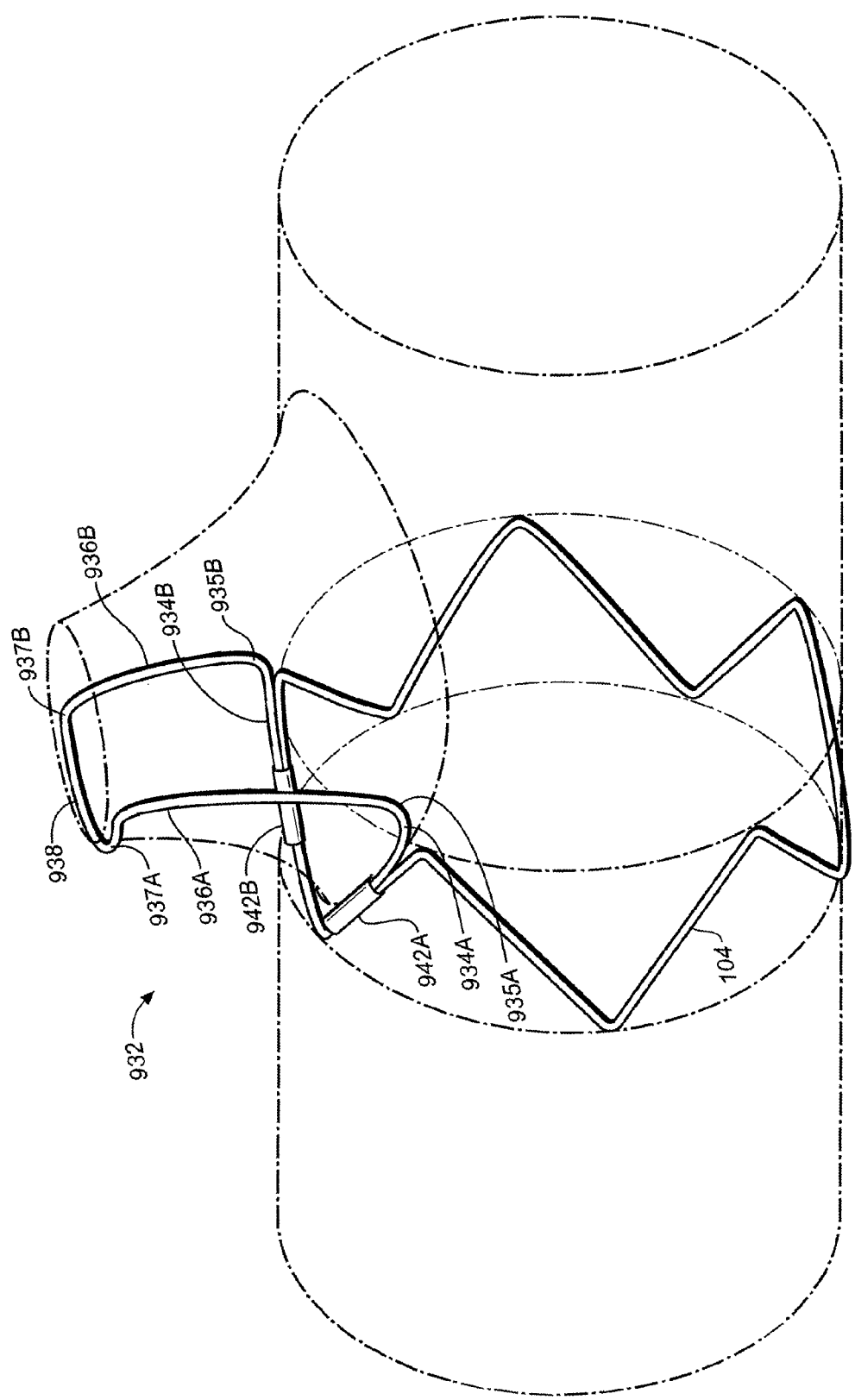

In another embodiment hereof, the coupling deployment device may include two spring arms to more uniformly deploy the mobile external coupling into the target branch vessel. Coupling deployment device 932 is similar to coupling deployment device 132 shown in FIG. 1 and the similar reference numerals have been used to identify the similar parts. Specifically, referring to FIG. 9, FIG. 10A, and FIG. 10B, coupling deployment device 932 includes a first base segment 934A, a first spring arm 936A, a second base segment 934B, a second spring arm 936B, and a semicircular apical segment 938 coupled to ring 122 of mobile external coupling 120. In an embodiment, coupling deployment device 932 is a unitary structure formed out of a single piece of material and includes four integral turns or hinges: a first hinge 935A between first base segment 934A and first spring arm 936A, a second hinge 937A between first spring arm 936A and apical segment 938, a third hinge 935B between second base segment 934B and second spring arm 936B, and a fourth hinge 937B between second spring arm 936B and apical segment 938. In another embodiment, the spring arms may be separate components that are attached to the base and apical segments by any suitable manner known in the art. Base segments 934A, 934B are coupled to a circumferential stent 104 of stent-graft 100 via a first crimp 942A and a second crimp 942B, respectively. Spring arms 937A, 937B each extend generally longitudinally along mobile external coupling 120 and are located on opposing sides of mobile external coupling 120 to symmetrically deploy the mobile external coupling. In addition to more symmetrical deployment, a smaller diameter wire in the range of 0.008 inch in diameter may be used with coupling deployment device 932 having double spring arms 936A, 936B to achieve the same extension or "pop-out" force to pop out mobile external coupling 120 from body 107 of stent-graft 100 when released from a sleeve during delivery to a target site when compared to the wire of a coupling deployment device having a single spring arm. In an example, a coupling deployment device with two spring arms as shown in FIGS. 9, 10A, and 10B was provided on a mobile external coupling having a height of 12 mm and a base of 15×20 mm. The coupling deployment device was made of NiTi wire with diameter of 0.012 inch. The mean maximum deployment or pop-out force was approximately 144 grams-force (1.412 Newtons or 0.317 pounds-force). Further, the force required to move mobile external coupling in a direction transverse to its longitudinal axis 144 (i.e., a side deflection force) was approximately 3.78 to 3.98 pounds-force (1714.6 to 1805.3 grams-force or 16.8 to 17.7 Newtons). Those of ordinary skill in the art would appreciate that this is just an example for this particular design, and that the forces may be varied in order to vary the forces noted.

Referring now to FIGS. 11-16, another embodiment of an endoluminal stent-graft including a mobile external coupling with a coupling deployment device is shown. Similar to the embodiments described above, stent-graft 1100 includes graft material 102 coupled to a plurality of circumferential stents 104. Stent-graft 1100 further includes a frustoconically shaped mobile external coupling 120 disposed on an outside surface of stent-graft 1100 at an opening in graft material 102. Mobile external coupling 120 includes base 124, top 126, and lumen 130 extending therethrough as described above. However, in the embodiment of FIGS. 11-16, the coupling deployment device is not coupled to one of the circumferential stents 104. Instead, a coupling deployment device 1132 includes a support or base stent 1104 disposed around body 107 of stent-graft 1000 adjacent mobile external coupling 120. Base stent 1104 extends around a significant portion of the circumference of body 107 of stent-graft 1100, but does not encircle or extend completely around body 107. Rather, base stent 1104 includes an extension or integral coupling deployment device 1132 that is coupled to mobile external coupling 120 to extend mobile external coupling 120 away from body 107 and into the ostium of the target branch vessel during deployment to ensure that mobile external coupling 120 fully extends into the ostium. In the embodiment shown in FIG. 11 base stent 1104 is coupled to an outside surface of graft material 102 and may extend around approximately between 50% and 90% of the circumference of body 107 of stent-graft 1100. In one embodiment, base stent 1104 extends around approximately 75% of the circumference of body 107. However, base stent 1104 may alternatively be coupled to an inside surface of graft material 102. Base stent 1104 may be any conventional stent configuration. As shown, base stent 1104 is preferably made from a shape memory material, such as thermally treated stainless steel or nickel-titanium alloy (nitinol), and is formed into a zig-zag configuration.

Referring to FIGS. 13-16, integral coupling deployment device 1132 includes first and second spring arms 1136A, 1136B, respectively, and a semicircular apical segment 1138. A first hinge or turn 1137A is integrally formed between first spring arm 1136A and apical segment 1138, and a second hinge or turn 1137B is integrally formed between second spring arm 1136B and apical segment 1138. Spring arms 1136A, 1136B are formed into a zig-zag or sinusoidal configuration as shown. Spring arms 1136A, 1136B are shape set into a configuration with such that when attached to mobile external coupling 120, mobile external coupling 120 will be in an extended configuration.

Base stent 1104 and integral coupling deployment device 1132 are a unitary structure formed out of a single piece of material. In particular, base stent 1104 and integral coupling deployment device 1132 are formed from a wire 1133 that may be solid or hollow and have a circular cross-section. In an embodiment, wire 1133 has a diameter between about 0.008 inch and 0.016 inch. In other embodiments, the cross-section of wire 1133 may be an oval, square, rectangular, or any other suitable shape. Base stent 1104 and integral coupling deployment device 1132 are continuously connected via two hinges or turns. Specifically, a first hinge or turn 1135A connects base stent 1104 and first spring arm 1136A of integral coupling deployment device 1132, and a second hinge or turn 1135B connects base stent 1104 and second spring arm 1136B of integral coupling deployment device 1132. The zig-zag or sinusoidal configuration of spring arms 1136A and 11336B extends in the direction of the length of mobile external coupling 120, or extends generally in the direction of longitudinal axis 1144 of mobile external coupling 120, and thus spring arms 1136A, 1136B are herein considered to extend generally longitudinally along mobile external coupling 120. However, spring arms 1136A, 1136B may have alternative configurations that extend generally longitudinally along mobile external coupling 120, such as substantially straight or slightly curved around the conical surface of mobile external coupling 120.

When mobile external coupling 120 and coupling deployment device 1132 coupled thereto are loaded in a delivery system, spring arms 1136A, 1136B of coupling deployment device 1132 are collapsed along the longitudinal axis of stent-graft 1100 at hinges 1135A, 1135B. Strain ensuing from being collapsed or packed concentrates at first and second hinges 1135A, 1135B, as well as at first and second hinges 1137A, 1137B of coupling deployment device 1132. Energy is accordingly stored within the shape memory material of wire 1133 at hinges 1135A, 1135B, 1137A, 1137B to result in a high release or deployment force of coupling deployment device 1132. Upon release from the delivery system, the stored energy is released such that wire 1133 recovers its annealed shape and spring arms 1136A, 1136B extend mobile external coupling 120 into the ostium of the target branch vessel to allow for easy antegrade cannulation of the branch vessel. Mobile external coupling 120 thus self expands or pop outs to extend away from the body of stent-graft 1100. This prevents bunching or collapse of the mobile external coupling 120 when released from the delivery system. In an example, a coupling deployment device as shown in FIGS. 11-16 was provided on a mobile external coupling having a height of 12 mm and a base of 15×20 mm. The coupling deployment device was made of NiTi wire with a diameter of 0.012 inch. The mean maximum deployment or pop-out force was approximately 110 grams-force (1.08 Newtons or 0.243 pounds-force). Further, the force required to move mobile external coupling in a direction transverse to its longitudinal axis 144 (i.e., a side deflection force) was approximately 2.21 to 3.42 pounds-force (1002.4 to 1551.3 grams-force or 9.83 to 15.21 Newtons). Those of ordinary skill in the art would appreciate that this is just an example.

Figure 11:
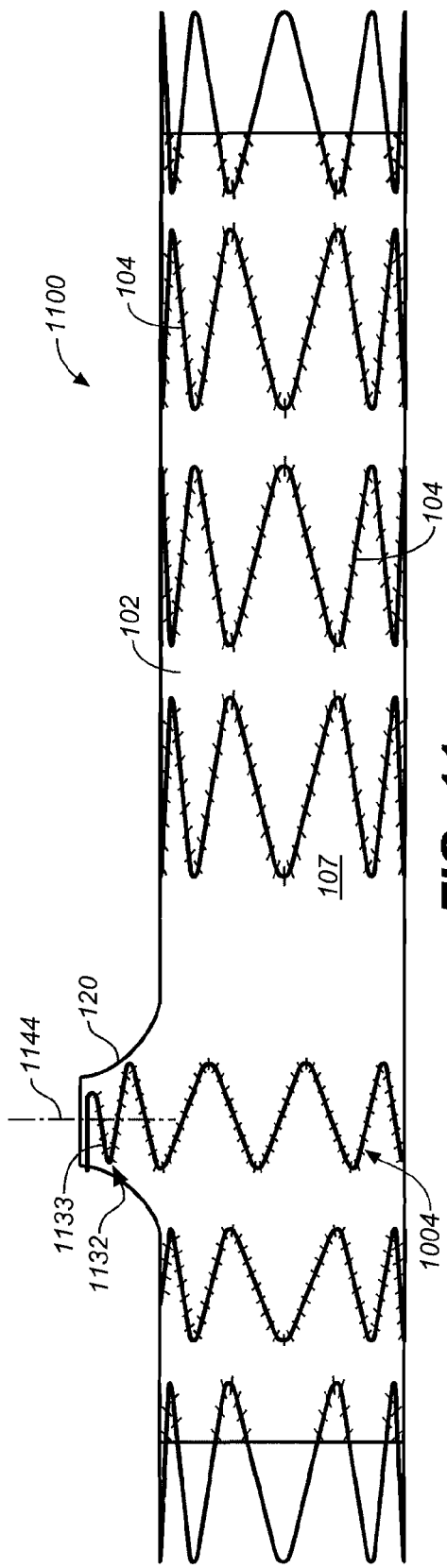
FIG. 11 is a schematic side view of an endoluminal stent-graft having an integral coupling deployment device illustrating another embodiment.
Figure 12:
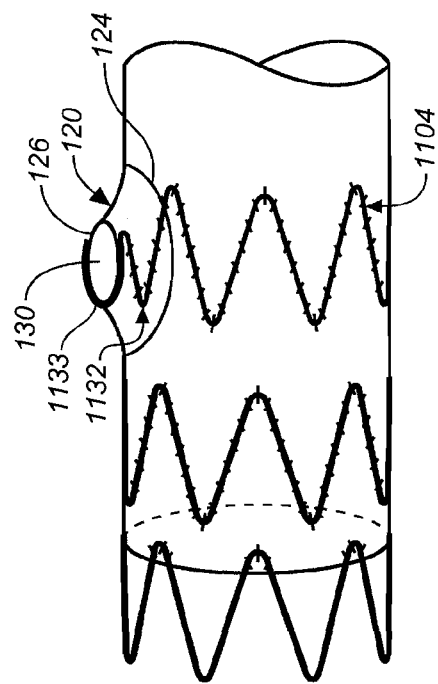
FIG. 12 is a schematic close up illustration of a portion of the endoluminal stent-graft of FIG. 11.
Figure 16:
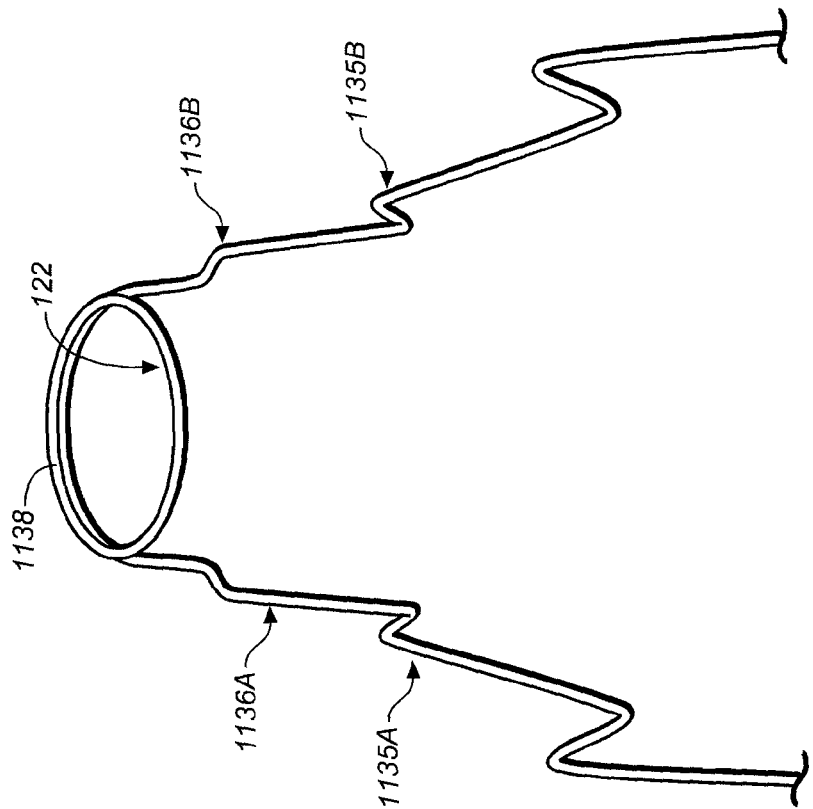
FIGS. 15 and 16 are images of the coupling deployment device of FIG. 11 coupled to a wire ring at the top thereof.
Figure 15:
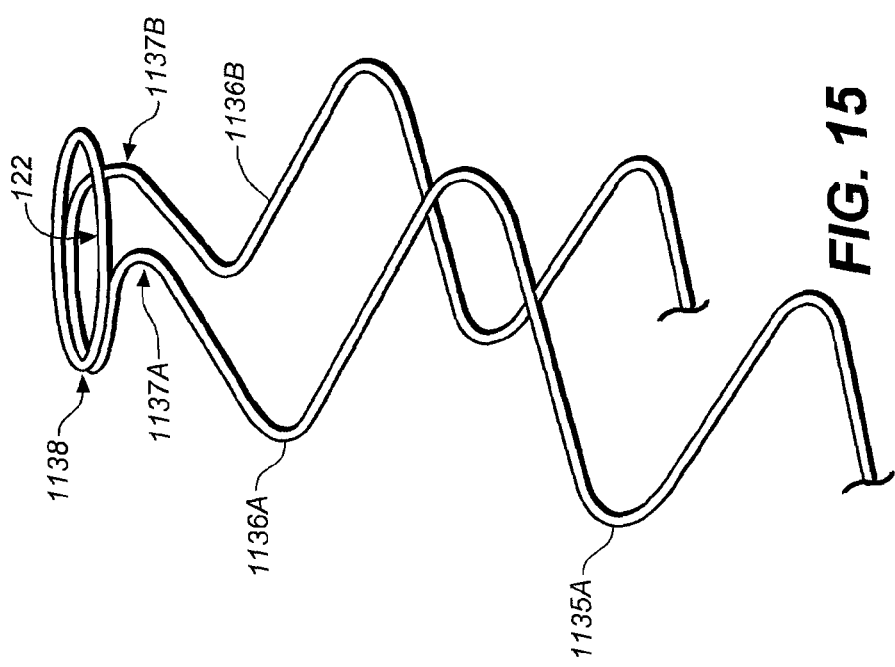

As shown in FIGS. 14 and 15, apical segment 1138 of integral coupling deployment device 1132 may be coupled to ring 122. Ring 122 and apical segment 1138 may then be coupled to mobile external coupling 120 as described in above embodiments. In an embodiment, ring 122 is of a smaller gauge wire than wire 1133 in order to control or limit the deployment force of integral coupling deployment device 1132. Alternatively, ring 122 may be omitted and semicircular apical segment 1138 alone may be coupled to mobile external coupling 120 as shown in FIGS. 11-12.

Base stent 1104 and integral coupling deployment device 1132 may be formed using any of a number of different methods that would be apparent to one skilled in the art. For example, base stent 1104 and integral coupling deployment device 1132 may be formed by winding a wire or ribbon around a mandrel to form a zig-zag pattern like that described above and then welding or otherwise mechanically connecting the two ends thereof. If desired, ring 122 may then be crimped onto apical segment 1138 of integral coupling deployment device. Alternatively, laser or chemical etching or another method of cutting a desired shape out of a solid stock material or tubing may also be used to form base stent 1104 and integral coupling deployment device 1132. If desired, ring 122 may then be crimped onto apical segment 1138 of integral coupling deployment device. Alternatively, if laser cutting or other similar method is utilized, ring 122 may be integrally formed with base stent 1104 and integral coupling deployment device 1132. The width of the material of apical segment 1138 and/or ring 122 may be laser cut smaller than the width of the material of base stent 1104 if it is desired to control or limit the deployment force of integral coupling deployment device 1132.

Various examples of particular wire sizes and configurations have been provided above, with "pop-out" force and side deflection force data provided. Those of ordinary skill in the art would recognize that the forces may be varied by varying the wire sizes, the mobile external coupling graft material, the connection between the coupling deployment device and graft material, and other factors. Factors for choosing the appropriate design include: 1) that the mobile external coupling deploy into the ostium of the branch vessel; and 2) that the mobile external coupling provide sufficient compliance in the face of side forces to permit the mobile external coupling to bend to reach the ostium if the mobile external coupling is not perfectly aligned with the ostium. If either the side compliance is too small, or the "pop-out" force is too large, the mobile external coupling may not perform optimally and may result in poor deployments. A desirable range for the deployment or "pop-out" force is between 80 to 120 grams-force and a desirable range for the side deflection force is between 0.8 and 1.2 pounds-force (measure at the top end of a 12 mm high cuff whose top has been deflected transversely 0.15 inches).

FIGS. 17-27 show an example of a delivery system that can be used to deliver stent-graft 100 to the target location within a vessel. FIG. 17 is an illustration of a stent-graft delivery system 200 with stent-graft 100 disposed therein. Stent-graft delivery system 200 includes a distal portion 201 and a proximal portion 250. Distal portion 201 is preferably used to load and deliver stent-graft section 100. Proximal portion 250 includes components such as those found conventionally in catheter delivery systems.

The components of the proximal portion 250 of the delivery system 100 may include those shown in FIGS. 17 and 18, although additional and/or alternative components are also contemplated. In particular, proximal portion 250 of delivery system 200 includes a Touhy Borst adaptor 266, a stent capture slider 268, a sideport extension 262, a side lumen access 264, a rear grip 260, a screw gear 258, an external slider 254 including a button 256, a front grip 252, and a strain relief 269. One or more hemostatic valves may be provided in front grip 106, for example, as described in U.S. Published Patent Application Publication No. 2006/0229561, commonly assigned with the present application, which is incorporated herein by reference in its entirety. The delivery system 200 as described is generally similar to the Xcelerant Delivery System, sold by Medtronic, Inc., but may be any conventional therapy delivery system, with modifications noted in detail below. Delivery system 200 is generally a single use, disposable device with the stent-graft 100 mounted on within distal end 201 of the delivery system 200.

Figure 19:
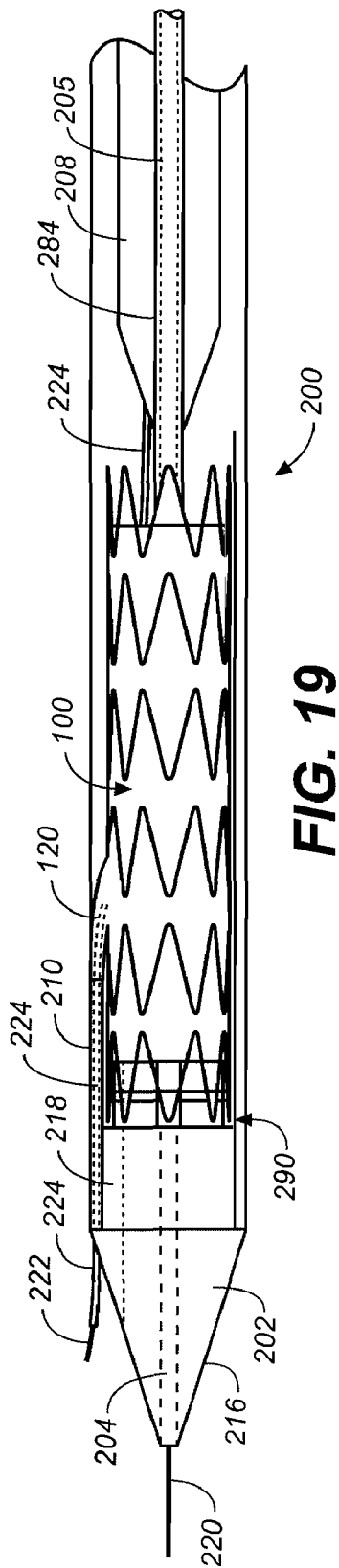
FIG. 19 is a schematic illustration of a distal portion of the stent-graft delivery device of FIG. 17 with a stent-graft disposed therein.
Figure 21:
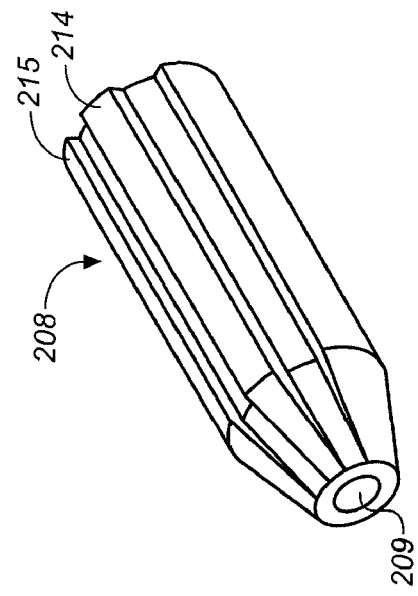
FIG. 21 is a schematic illustration of a stent stop including grooves for the side tube.
Figure 20:
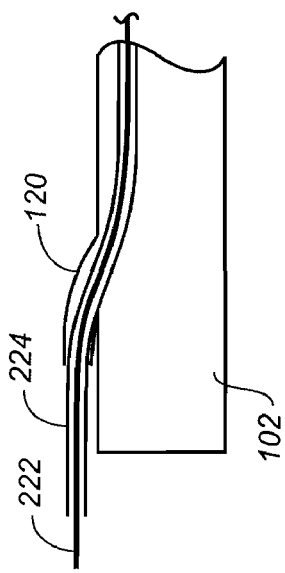
FIG. 20 is a schematic illustration of a stent graft with a side tube for the second guide wire extending through a lumen of the tubular body of the stent-graft and through a lumen of the mobile external coupling.

FIG. 19 is a schematic cross sectional view of the distal portion 201 of delivery system 200. Distal portion 201 includes a tapered tip 202 that is flexible and able to provide trackability in tight and tortuous vessels. Other tip shapes such as bullet-shaped tips could also be used. The tip 202 includes a lumen 204 disposed therethrough for accommodating a first guide wire 220.

The tapered tip 202 includes a tapered outer surface 216 that gradually decreases in diameter in a distal direction. More particularly, tapered outer surface 216 has a first diameter at a proximal end and gradually decreases in diameter distally, i.e., in the direction away from the operator. Tapered outer surface 216 further includes a groove 218, as best seen in FIG. 23, for accommodating a second guide wire 222 within a lumen of a side tube 224. A shoulder 212 reduces the diameter of a proximal portion of tip 202 to provide a sleeve landing surface 226. Shoulder 212 is generally annular and perpendicular to a longitudinal axis of stent-graft delivery system 200.

An outer sleeve 210 of stent-graft delivery system 200 extends over the outer cylindrical surface of sleeve landing surface 226 and abuts against shoulder 212 when the stent-graft delivery system 200 is in a pre-deployment configuration, as shown in FIG. 19. Stent-graft delivery system 200 further includes a stent capture system 290 that captures and holds an end of stent-graft 100, as explained in more detail below.

Stent-graft delivery system 200 also includes an inner tube 205 that is coupled to a tip lumen 204 such that first guide wire 220 may extend the length of delivery system 200. A stent capture tube 284 of stent capture system 290 surrounds inner tube 205, as explained in more detail below. A stop 208 may be located at a distal end of stent-graft 100 when stent-graft 100 is loaded onto the delivery system 200. Stop 208 can prevent longitudinal movement of stent-graft 100 as outer sleeve 210 is retracted or otherwise removed to release stent-graft 100. Stop 208 can include a lumen 209 through which stent capture tube 284 and inner tube 205 are disposed. Stop 208 further can include grooves 214 disposed between landings 215. Stop 208 in this embodiment extends proximally along the length of the delivery system 200. Side tube 224 may be disposed in any of the grooves 214 and extend proximally the length of the delivery system to be control at proximal portion 250 through side lumen access 264. Stent-graft 100 is disposed within outer sleeve 210 in a compressed or delivery configuration wherein the diameter of stent-graft 100 is reduced such that it can be inserted through the vasculature.

Second guide wire 222 extends through stent-graft delivery system 200 through a lumen of side tube 224, which extends through lumen 116 of stent-graft 100, through lumen 130 of mobile external coupling 120, between outer sleeve 210 and body 107, and out a distal end of outer sleeve 210 through groove 218 of tip 202. In the delivery or compressed configuration, mobile external coupling 120 may be folded as shown schematically in FIGS. 19 and 20.

Stent capture system 290 is shown in FIG. 22. Stent capture system 290 includes a spindle 270 and a stent capture assembly 280. Stent capture system 290 may be similar to or identical to stent capture system described in U.S. Published Application Publication No. 2009/0276027, published Nov. 5, 2009, which is incorporated by reference herein in its entirety.

Spindle 270 shown in FIG. 22 is fixed to inner shaft 205 adjacent a proximal end of tip 202. Spindle 270 includes a lumen (not shown) through which inner shaft is disposed. Spindle 270 may also be slidable relative to inner shaft 205, for example, as described in U.S. Published Application Publication No. 2009/0276027. Spindle 270 includes a number of spindle pins 274 disposed around the circumference of the spindle body. A spindle groove 272 is formed between each pair of adjacent spindle pins 274. A single stent crown (not shown) of proximal anchor stent 112 wraps around each spindle pin 274 and is held in place by a stent capture fitting arm 286 of the stent capture assembly 280 during stent-graft delivery. When the stent capture assembly 280 is refracted, the stent crowns are freed from the spindle pins 274 and proximal anchor stent 112 expands into position in the vessel. The spindle 270 can be made of any rigid and/or compliant biocompatible material and can be formed as a single unit and/or assembled from individual parts. Those skilled in the art will appreciate that the spindle 270 can made of any biocompatible material and can be formed as a single unit and/or assembled from individual parts. Other embodiments of spindle 270, as described for example in U.S. Published Application Publication No. 2009/0276027, may also be used.

Stent capture assembly 280 includes a stent capture fitting 282 and a stent capture shaft 284. The stent capture assembly 280 defines a stent capture assembly lumen (not shown) along its length through which inner shaft 205 can slide. The diameter of the stent capture assembly lumen is large enough that the inner shaft can slide within the stent capture assembly lumen. The stent capture shaft 284 advances the stent capture fitting 282 to hold the stent crowns wrapped around spindle pins 274 in place during delivery and initial deployment of stent-graft 100. Stent capture shaft 284 retracts the stent capture fitting 282 to release the proximal anchor stent 112 of the stent-graft 100 from the delivery diameter. The stent capture shaft 284 is long enough the reach through the vasculature from the stent graft deployment site in the vessel to the clinician. The proximal end of the stent capture shaft 284 is attached to stent capture slider 268 shown in FIGS. 17 and 18 for manipulation by the clinician during stent-graft delivery. Those skilled in the art will appreciate that the stent capture assembly 280 can made of any biocompatible material and can be formed as a single unit and/or assembled from individual parts. The stent capture shaft 284 may be constructed of a rigid plastic, such as PEEK polyetheretherketone, polyimide, nylon, or the like. The stent capture shaft 284 can alternatively be constructed of a flexible metal tube such as nitinol, stainless steel, or the like.

The stent capture fitting 282 in cooperation with the spindle 270, retains one end of the stent-graft during stent-graft delivery. In the illustrated embodiment, the stent capture fitting 282 includes a stent capture body 285 having a number of stent capture fitting arms 286 disposed around the circumference of the stent capture body 285. The stent capture body 285 defines a number of stent capture grooves 288 between each of the stent capture fitting arms 286 to receive the bare stent crowns. The stent capture fitting arms 286 can be substantially parallel to the central axis of the stent capture fitting 282, i.e., the axis along the stent capture shaft 284. In other embodiments, the stent capture fitting arms 286 can curve toward or away from the axis of the stent capture fitting 282 as desired for a particular purpose. When the stent capture fitting 282 is retracted, the stent capture fitting arms 286 release the bare stent crowns, and the proximal anchor stent 112 expands into position in the vessel. The stent capture fitting 282 can be made of any rigid and/or compliant biocompatible material and can be formed as a single unit and/or assembled from individual parts. The stent capture fitting may be fabricated from a variety of materials. This may include rigid plastic materials such as PEEK polyetheretherketone, polycarbonate, or the like, and may also include metals such as stainless steel. In one embodiment, a hard plastic or highly polished metal is desirable for the stent capture fitting 282 to avoid damage to the stent surface which is in contact with the stent capture fitting 282. The stent capture fitting 282 can be fastened to the stent capture shaft 284 by bonding the two with adhesive or threading the two components together. The stent capture fitting 282 may alternatively be insert molded directly on the stent capture shaft 284.

Figure 24:
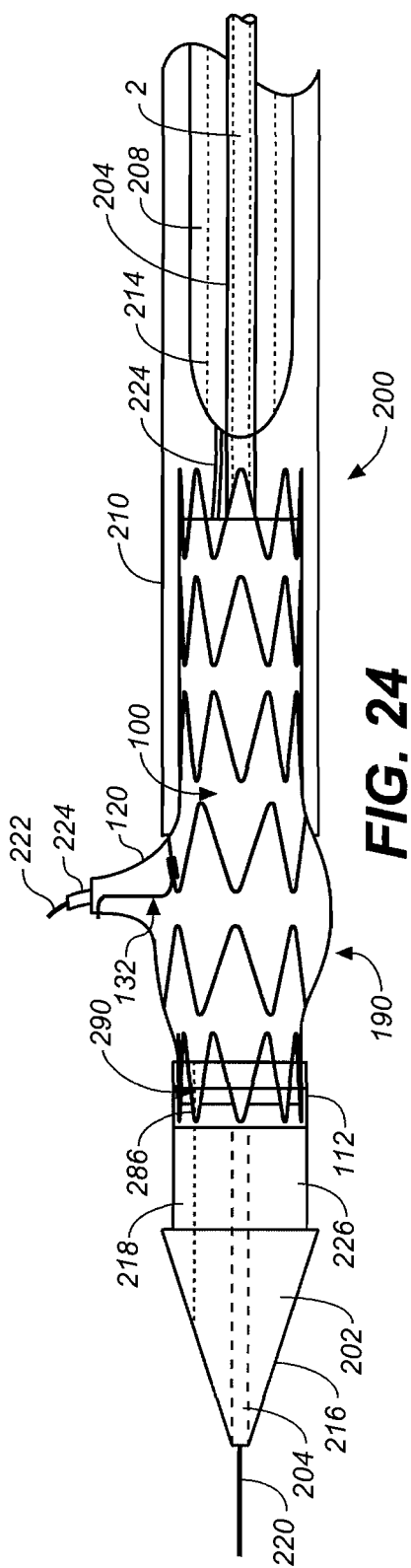
Figure 24A:
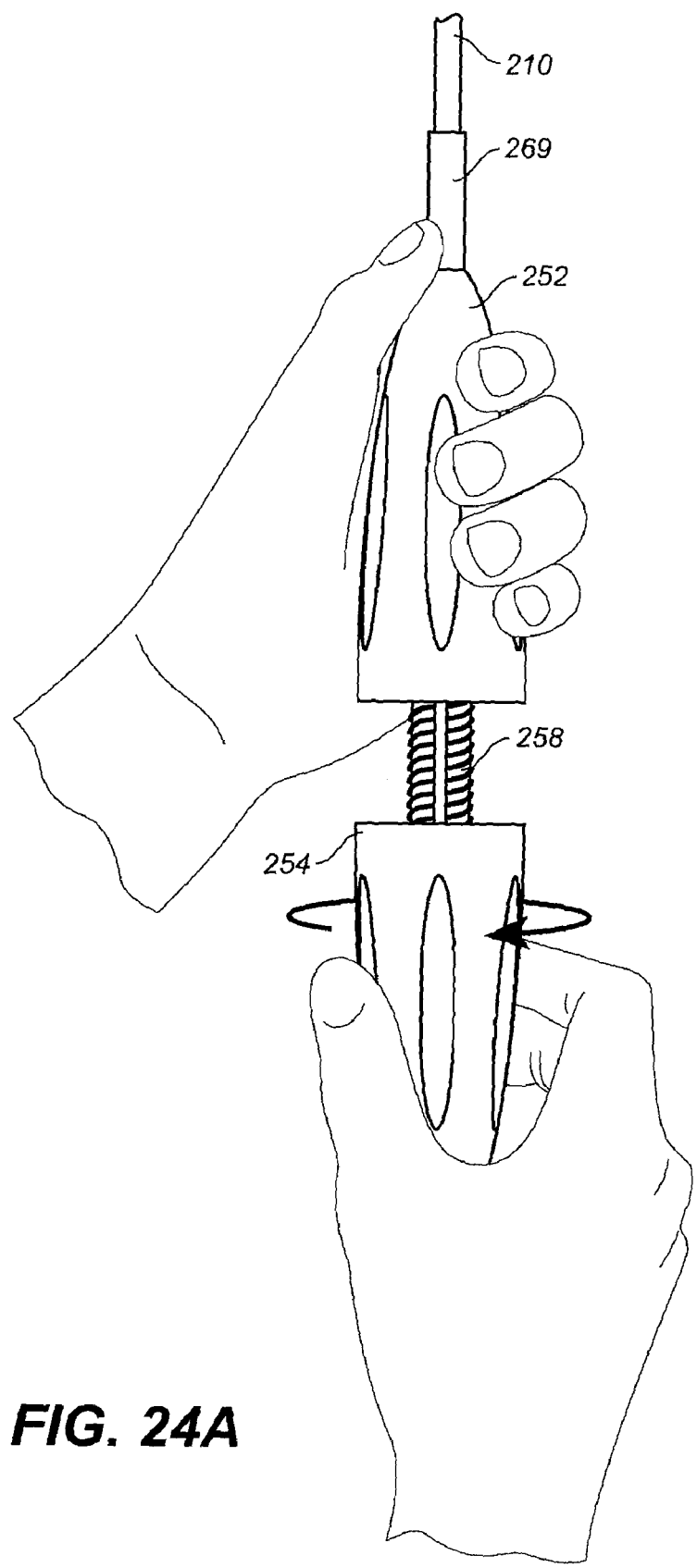

Outer sleeve 210 is a hollow tube and defines a lumen therein within which stent-graft 100, stent capture system 290, side shaft 224 and inner tube 205 are disposed in the delivery configuration shown in FIG. 19. In a first step for deploying the stent-graft, outer sleeve 210 is moved proximally, i.e. retracted, relative to inner tube 205 to a position adjacent the mobile external coupling 120, as shown in FIG. 24. Outer sleeve 210 may be retracted by retracting external slider 254 by counter-clockwise rotational movement, as shown in FIG. 24A. This rotational movement provides a slower refraction of outer sleeve 210 a controlled release of the proximal portion of stent-graft 100, as shown in FIG. 24. Due to stent capture assembly 290 holding proximal anchor stent 112 of the stent-graft 100 in the radially compressed delivery configuration, and the relatively short distance to the mobile external coupling 120, the portion 190 of the stent that is free to expand is relatively short, as shown in FIG. 24. However, as also shown in FIG. 24, mobile external coupling 120 is no longer constrained by outer sleeve 210, and the energy stored in coupling deployment device 132 (or coupling deployment device 132', 932, or 1132) is released such that mobile external coupling 120 pops-out from body 107 and into the ostium of the branch vessel.

The side tube 224 may be removed by withdrawing it proximally from side lumen access 264 at the proximal portion 250 of the delivery system 200. Second guide wire 222 may be manipulated to adjust the location or orientation of mobile external coupling 120. Optionally, side tube 224 may remain in place while mobile external coupling 120 is adjusted.

Figure 25:
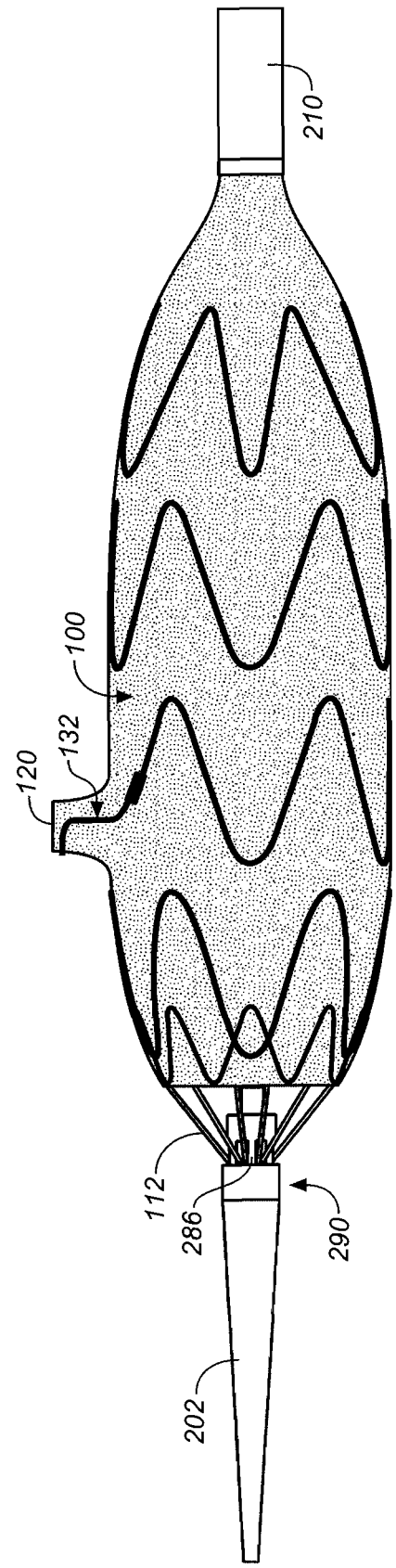
Figure 25A:
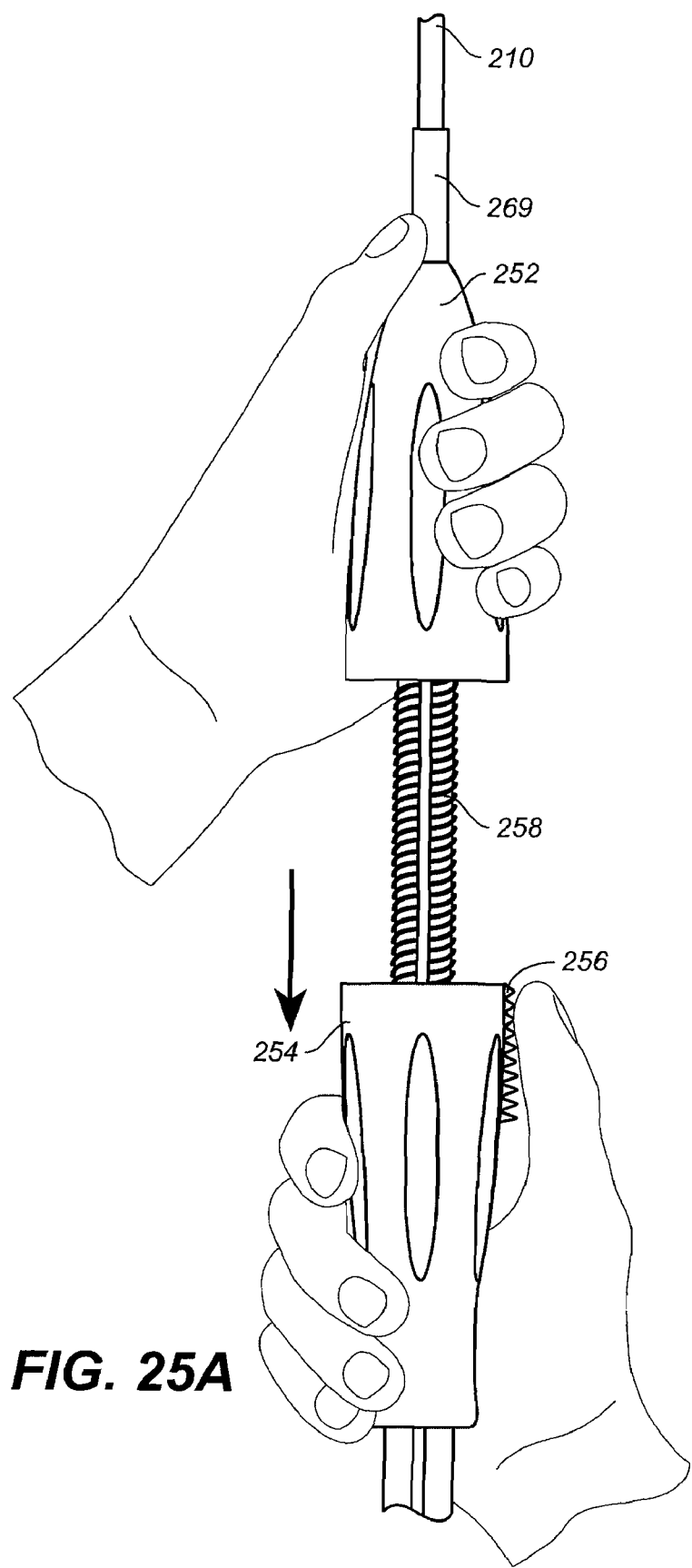

After mobile external coupling 120 is properly located in the ostium of the branch vessel, outer sleeve 210 may be further refracted, as shown in FIG. 25, by further retracting external slider 254. FIG. 25 shows outer sleeve 210 further refracted, but not fully retracted, as distal anchor stent 114 of stent-graft 100 remains disposed within outer sleeve 210. When outer sleeve 210 is fully refracted, as shown in FIG. 26, the entire stent-graft body, except for the portion retained by stent capture assembly 290, is in the radially expanded or deployed configuration. This further retraction of external slider 254 may be done more quickly than the initial controlled retraction by pressing trigger 256 and sliding external slider 254, as shown in FIG. 25A, rather than rotating external slider 254. However, those of ordinary skill in the art would recognize that the initial retraction and further retraction of external slider 254 may each be accomplished through rotation of external slider 254 or sliding of external slider 254. Further, other methods and devices for retracting outer sleeve 210 could be utilized, as known to those of ordinary skill in the art.

After outer sleeve 210 is fully retracted, stent capture slider 268 may be retracted proximally such that stent capture assembly 280 moves proximally away from spindle 270. Stent capture fitting arms 288 thereby release proximal anchor stent 112 such that proximal anchor stent expands, as shown in FIG. 27.

The stent-graft delivery system 200 described herein is only an example of a delivery system that can be used to delivery and deploy stent-graft 100 and many other delivery systems known to those skilled in the art could be utilized. For example, stent-graft 100 could be mounted onto a balloon to be expanded when at the target site. Other stent-graft-delivery systems, for example and not by way of limitation, the delivery systems described in U.S. Published Patent Application Publication Nos. 2008/0114442 and 2008/0262590 and U.S. Pat. No. 7,264,632, and U.S. patent application Ser. Nos. 12/425616 and 12/425628, each filed Apr. 17, 2009, each of which is incorporated herein by reference in its entirety, may be utilized to deliver and deploy stent-graft 100.

FIGS. 28-33 schematically show a method of delivering stent-graft 100 to a target site in a main vessel and a method of delivering a branch stent-graft to branch vessel. Although FIGS. 26-31 describe a method for delivering a stent-graft having a mobile external coupling 120 with coupling deployment device 132, the method can be used to deliver a stent graft having coupling deployment device 132' (FIG. 8), coupling deployment device 932 (FIGS. 9, 10A, 10B), or coupling deployment device 1132 (FIGS. 11-16) as well. In the example described herein, the stent-graft 100 is delivered and deployed into the aorta 300. Portions of the aorta 300 include the ascending aorta 302, the aortic arch 304, and the descending aorta 306. Branching from the aortic arch are the brachiocephalic trunk 308, the left common carotid artery 314, and the left subclavian artery 316. The brachiocephalic trunk branches into the right subclavian artery 310 and the right common carotid artery 312. An aneurysm 318 in the area of the aortic arch 304 can be difficult to bypass or exclude with a stent-graft because blood flow to the branch arteries must be maintained.

In the embodiment shown in FIGS. 28-33, the aneurysm is sufficiently close to brachiocephalic trunk 308 that the stent-graft 100 must extend between the brachiocephalic trunk 308 and the heart. In such a case and with a stent-graft 100 with only a single mobile external coupling 120, the mobile external coupling 120 is designed so as to be deployed into the brachiocephalic trunk 308 to perfuse the brachiocephalic trunk 308. Prior to the procedure for inserting stent-graft 100, surgical by-pass procedures installing bypass grafts or vessels (not shown) are performed to connect the right common carotid artery 312 to the left common carotid artery 314 and the left common carotid artery to the left subclavian artery 316. Such surgical bypass procedures may be performed one to two weeks prior to insertion of the stent-graft, and present significantly less complications and risk than a surgical solution to repair an aneurysm 318 in the aortic arch. In this manner, maintaining perfusion to the brachiocephalic trunk 308, and hence the right common carotid artery 312, maintains perfusion to the left common carotid artery 314 and the left subclavian artery 316 Thus, the openings (or ostia) to these branch vessels directly from the aortic arch may be blocked by stent-graft 100. In the alternative, multiple mobile external couplings 120 may be provided in stent-graft 100. Further, if the aneurysm only affects the left common carotid artery 314 and the left subclavian artery 316, only one by-pass between the left common carotid artery 314 and the left subclavian artery needs to be performed, and then a stent-graft with a single mobile external coupling 120 can be utilized to perfuse the left common carotid artery 314. Alternatively, in such a situation, a stent-graft with two mobile external couplings may be provided, one for each of the branch vessels noted. Accordingly, while the embodiment of stent-graft 100 in the method described below includes a single mobile external coupling 120 and the mobile external coupling is deployed in the brachiocephalic trunk 308, those skilled in the art would recognize that multiple mobile external couplings can be used and the mobile external coupling(s) may be deployed in other branch arteries.

Figure 28:
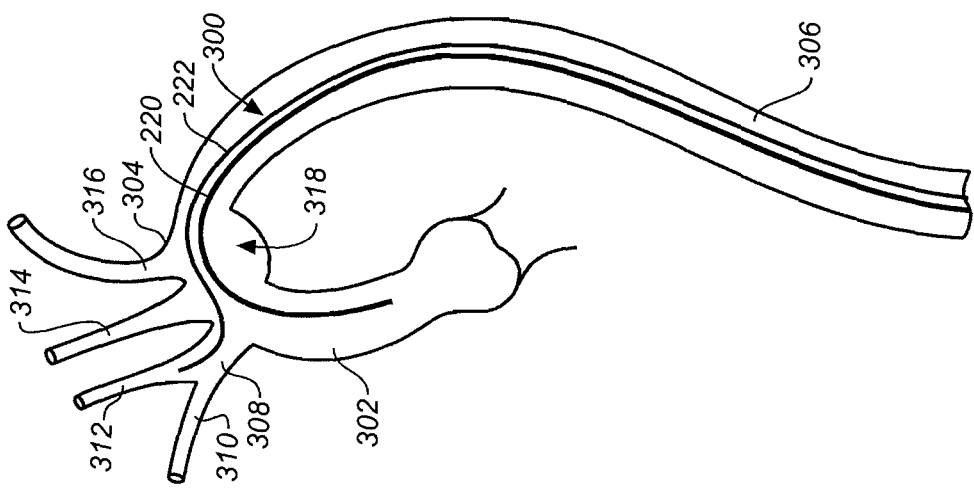

FIG. 28 shows the first guide wire 220 advanced through the descending aorta 306, through the aortic arch 304, and into the ascending aorta 302 and second guide wire 222 advanced through the descending aorta 306, through the aortic arch 304, and into brachiocephalic trunk 308. Guide wires 200, 222 are typically inserted into the femoral artery and routed up through the abdominal aorta, and into the thoracic aorta, as is known in the art. Second guide wire 222 may also be locked at its distal end so as to prevent second guide wire 222 from retracting. Access from the brachiocephalic artery or carotid artery may be used to lock second guide wire 222 at its distal or superaotric end, as is known to those of ordinary skill in the art as a through-and-through wire technique.

Figure 29:
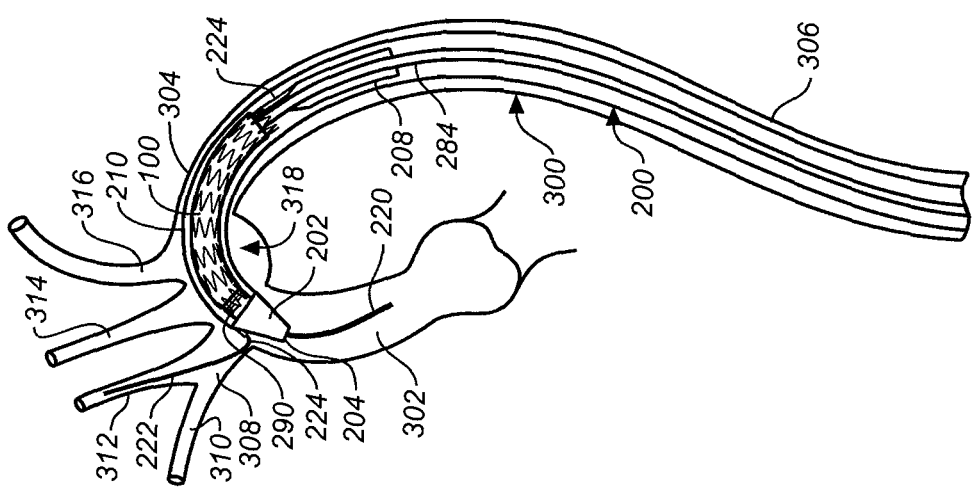

FIG. 29 shows stent-graft delivery system 200, with stent-graft 100 compressed therein, advanced over guide wires 220, 222 to the target location in the aortic arch 304. The location of the stent-graft delivery system 200 and/or the stent-graft 100 may be verified radiographically and delivery system 200 and/or stent-graft 100 may include radiopaque markers as known in the art.

Figure 30:
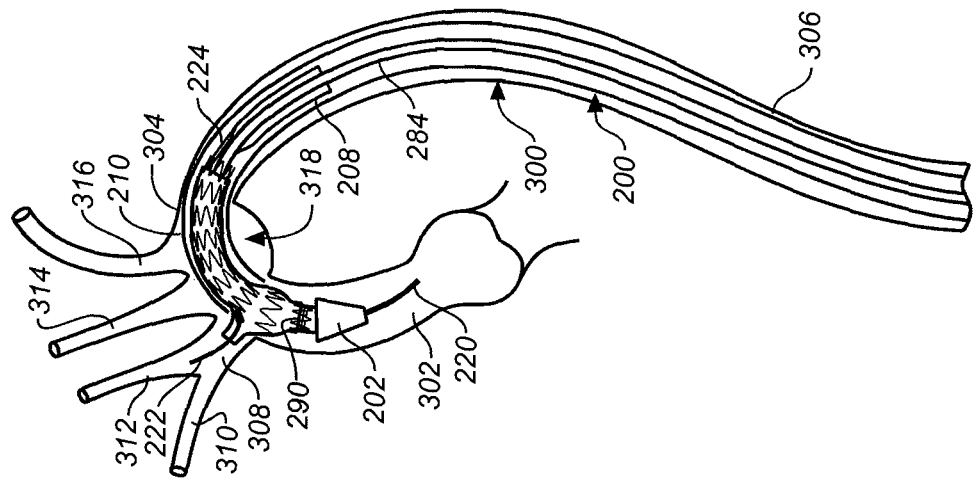
FIGS. 28-33 are schematic illustrations of progressive steps a method for delivering and deploying the stent-graft of FIG. 1 and a branch stent-graft to a target location.

After stent-graft delivery system 200 is in the location where the mobile external coupling 120 of the stent graft 100 is approximately aligned with the opening into the branch vessel, outer sleeve 210 is retracted proximally to a position adjacent to mobile external coupling 120 to release mobile external coupling 120, as shown in FIG. 30 (also shown in FIG. 24). Mobile external coupling 120 provides a positive outward force due to coupling deployment device 132 that reduces the possibility of the mobile external coupling 120 collapsing against or within body 107 after deployment. Delivery system 200 may then be moved and/or rotated to better align mobile external coupling 120 with the branch artery, in this case, the brachiocephalic trunk 308. Further, due to the configuration of mobile external coupling 120, even if it is not perfectly aligned with brachiocephalic trunk 308, the top of the mobile external coupling 120 may be moved to properly align its lumen opening with the lumen of the brachiocephalic trunk 308 without having to move the entire stent-graft 100. Force to adjust the position of the top of the mobile external coupling 120 can be created by pulling or pushing on the end of second guide wire 222. Coupling deployment device 132, as explained above, urges the distal end of mobile external coupling 120 distally away from the main graft and into the lumen of the branch vessel.

Figure 31:
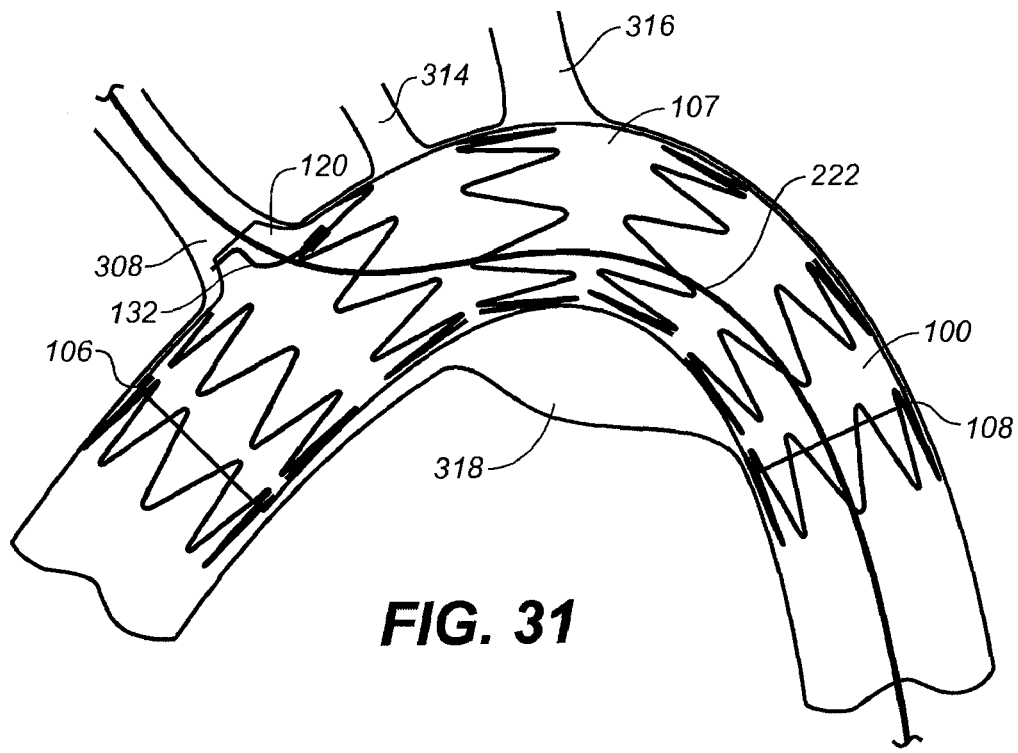
Figure 32:
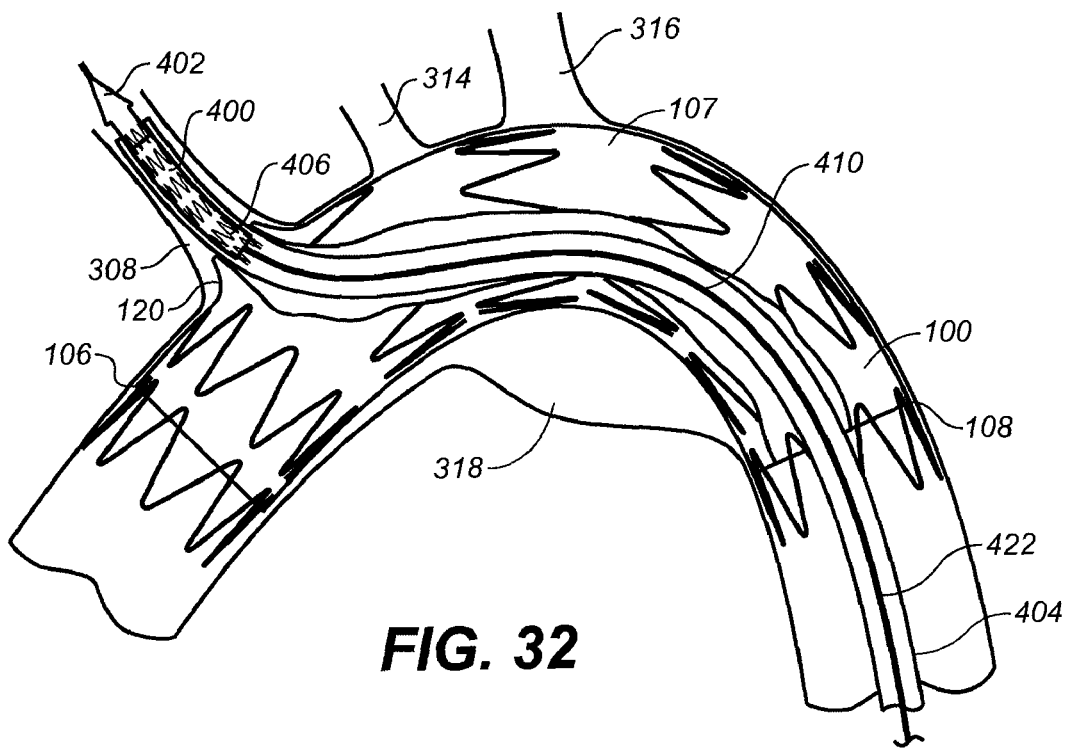
Figure 33:
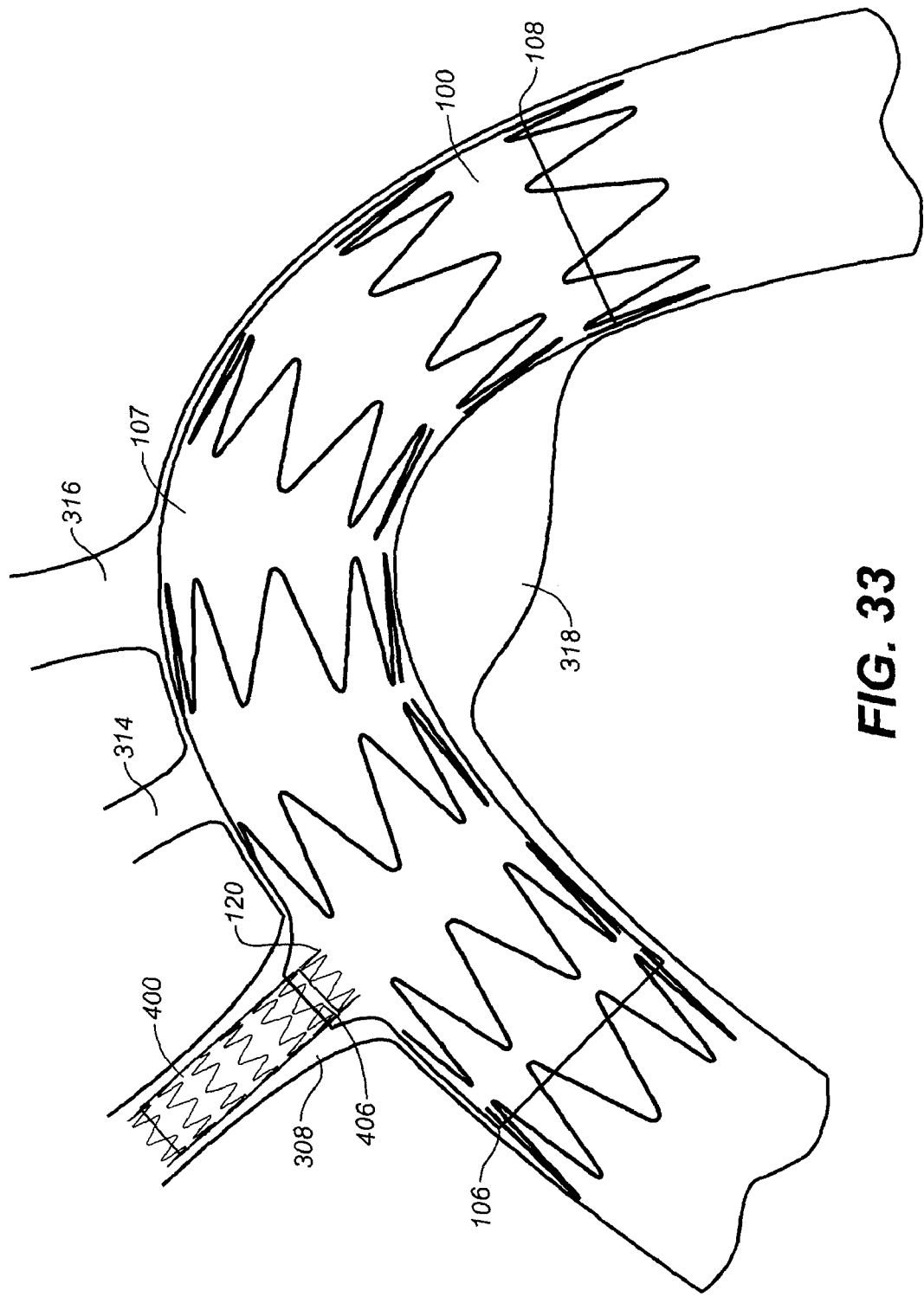

Once mobile external coupling 120 is deployed and in position in the brachiocephalic trunk 308, outer sleeve 210 may be further retracted as explained above with respect to FIGS. 25, 26 and 25A, thereby deploying the main body of the stent graft 100, as shown in FIGS. 25 and 26. The stent capture fitting 282 is then retracted proximally to release proximal anchor stent 112 of stent 100 to fully release stent-graft 100, as shown in FIGS. 27 and 31. Once mobile external coupling 120 and stent-graft 100 are deployed, delivery system 200 may be removed. Second guide wire 222 may remain in place in brachiocephalic trunk 308 or may be replaced by another guide wire. A branch stent-graft delivery system 404 is advanced over second guide wire 222 and into brachiocephalic trunk 308, as shown in FIG. 32. Branch stent-graft delivery system includes a tip 402 and a sleeve (not shown), and contains therein a branch stent-graft 400. Branch stent-graft delivery system 404 and branch stent-graft 400 may be conventional. Branch stent-graft delivery system 404 is advanced into brachiocephalic trunk 308 such that a proximal portion 406 of branch stent-graft 400 remains inside of mobile external coupling 120. The sleeve constraining branch stent-graft 400 is then retracted proximally, thereby releasing branch stent-graft 400 from delivery system 404. The delivery system 404 is then withdrawn, as shown in FIG. 33. Because proximal portion 406 of branch stent-graft 400 is disposed within mobile external coupling 120 when branch stent-graft 400 is expanded, proximal portion 406 necks (narrows) at the top 126 of mobile external coupling 120 to conform with an inside surface of mobile external coupling 120.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. It will also be understood that each feature of each embodiment discussed herein, and of each reference cited herein, can be used in combination with the features of any other embodiment. All patents and publications discussed herein are incorporated by reference herein in their entirety.

What is claimed is:

1. An endovascular prosthesis comprising:
a tubular body having a proximal end, a distal end, and a lumen disposed between the proximal and distal ends, the tubular body including a body graft material and a plurality of body stents coupled to the body graft material;
a mobile external coupling including an extended configuration wherein the mobile external coupling extends outwardly from the tubular body, wherein the mobile external coupling includes a base coupled to the tubular body, a top spaced from the tubular body, and a coupling lumen disposed between the base and the top, wherein the coupling lumen is in flow communication with the body lumen and wherein the mobile external coupling includes a coupling graft material; and
a coupling deployment device coupled to the mobile external coupling, wherein the coupling deployment device is also coupled a base stent disposed around at least a portion of the tubular body, and wherein the coupling deployment device extends generally longitudinally along the mobile external coupling in the extended configuration,
wherein the mobile external coupling and coupling deployment device include a collapsed configuration wherein the mobile external coupling and coupling deployment device are collapsed against an outside surface of the tubular body, and wherein the coupling deployment device is configured to store energy in the collapsed configuration such that when released from the collapsed configuration, the coupling deployment device provides an extension force to extend the mobile external coupling into the extended configuration.

2. The prosthesis of claim 1, wherein the coupling graft material is an extension of the body graft material.

3. The prosthesis of claim 1, wherein the coupling graft material is attached to the body graft material with sutures.

4. The prosthesis of claim 1, wherein the base is generally elliptical in shape and the top is generally circular in shape.

5. The prosthesis of claim 1, wherein the coupling deployment device is formed from a shape memory material.

6. The prosthesis of claim 5, wherein the shape memory material is a nickel-titanium alloy.

7. The prosthesis of claim 6, wherein the coupling deployment device is made from a wire about 0.008 inch to 0.016 inch in diameter.

8. The prosthesis of claim 7, wherein the plurality of body stents are made from a shape memory material about 0.018 inch to 0.021 inch in diameter.

9. The prosthesis of claim 1, wherein the extension force is between 80 and 120 grams-force.

10. The prosthesis of claim 1, wherein the base stent is one of the plurality of body stents.

11. The prosthesis of claim 1, wherein the base stent extends around only a portion of the tubular body.

12. The prosthesis of claim 1, wherein the base stent and the coupling deployment device are integrally formed from a continuous wire.

13. The prosthesis of claim 12, wherein the integral base stent and coupling deployment device are formed from a shape memory nickel-titanium alloy wire about 0.008 inch to 0.016 inch in diameter.

14. The prosthesis of claim 1, wherein the mobile external coupling is generally frustoconically shaped.

15. An endovascular prosthesis comprising:
a tubular body having a proximal end, a distal end, and a lumen disposed between the proximal and distal ends, the tubular body including a body graft material and a plurality of body stents coupled to the body graft material;
a mobile external coupling including an extended configuration wherein the mobile external coupling extends outwardly from the tubular body, wherein the mobile external coupling includes a base coupled to the tubular body, a top spaced from the tubular body, and a coupling lumen disposed between the base and the top, wherein the coupling lumen is in flow communication with the body lumen and wherein the mobile external coupling includes a coupling graft material; and
a coupling deployment device coupled to the mobile external coupling, wherein the coupling deployment device is a continuous wire including a base segment coupled to one of the plurality of body stents and extending generally transverse to a longitudinal axis of the mobile external coupling, a spring arm coupled to the base segment and extending generally longitudinally relative to the mobile external coupling, and an apical segment coupled to the spring arm and extending around at least a portion of the top of the mobile external coupling in a circumferential manner,
wherein the mobile external coupling and coupling deployment device include a collapsed configuration wherein the mobile external coupling and coupling deployment device are collapsed against the tubular body, and wherein the coupling deployment device is configured to store energy in the collapsed configuration such that when released from the collapsed configuration, the coupling deployment device provides an extension force to extend the mobile external coupling into the extended configuration.

16. The prosthesis of claim 15, further comprising a first hinge coupling the base segment to the spring arm and a second hinge coupling the spring arm to the apical segment.

17. The prosthesis of claim 15, wherein the apical segment is semicircular and coupled to a stent ring located around the top of the mobile external coupling.

18. The prosthesis of claim 15, wherein an end of the apical segment is shaped into a hook.

19. The prosthesis of claim 15, wherein the apical segment is circular and coupled to the top of the mobile external coupling.

20. The prosthesis of claim 15, wherein the spring arm is substantially straight.

21. The prosthesis of claim 15, wherein the mobile external coupling is generally frustoconically shaped.

22. The prosthesis of claim 15, wherein the extension force is between 80 and 120 grams-force.

23. An endovascular prosthesis comprising:
a tubular body having a proximal end, a distal end, and a lumen disposed between the proximal and distal ends, the tubular body including a body graft material and a plurality of body stents coupled to the body graft material;

a mobile external coupling including an extended configuration wherein the mobile external coupling extends outwardly from the tubular body, wherein the mobile external coupling includes a base coupled to the tubular body, a top spaced from the tubular body, and a coupling lumen disposed between the base and the top, wherein the coupling lumen is in flow communication with the body lumen and wherein the mobile external coupling includes a coupling graft material; and a coupling deployment device coupled to the mobile external coupling, wherein the coupling deployment device is a continuous wire including a first base segment coupled a base stent extending at least partially around the tubular body, a first spring arm coupled to the first base segment and extending generally longitudinally relative to the mobile external coupling, a generally semicircular apical segment extending around the top of the mobile external coupling in a circumferential manner and having a first end coupled to the first spring arm, a second spring arm coupled to a second end of the apical segment and extending generally longitudinally relative to the mobile external coupling, and a second base segment coupled to the second spring arm and to the base stent, wherein the mobile external coupling and coupling deployment device include a collapsed configuration wherein the mobile external coupling and coupling deployment device are collapsed against the tubular body, and wherein the coupling deployment device is configured to store energy in the collapsed configuration such that when released from the collapsed configuration, the coupling deployment device provides an extension force to extend the mobile external coupling into the extended configuration.

24. The prosthesis of claim 23, further comprising a first hinge coupling the first base segment to the first spring arm, a second hinge coupling the first spring arm to the apical segment, a third hinge coupling the apical segment to the second spring arm, and a fourth hinge coupling the second spring arm to the second base segment.

25. The prosthesis of claim 23, wherein the first spring arm and the second spring arm are substantially straight.

26. The prosthesis of claim 23, wherein the base stent is one of the plurality of body stents.

27. The prosthesis of claim 23, wherein the base stent extends around only a portion of the tubular body.

28. The prosthesis of claim 27, wherein the base stent and the coupling deployment device are integrally formed from a continuous wire.

29. The prosthesis of claim 28, wherein the integral base stent and coupling deployment device are formed from a shape memory nickel-titanium alloy wire about 0.008 inch to 0.016 inch in diameter.

30. The prosthesis of claim 23, wherein the mobile external coupling is generally frustoconically shaped.

31. A method for excluding an aneurysm at a target location near a junction of a main vessel and a branch vessel, comprising the steps of:

delivering a main prosthesis in a compressed configuration to the target location in the main vessel, wherein the main prosthesis includes a tubular body and a mobile external coupling, the tubular body having a proximal end, a distal end, a body lumen disposed between the proximal and distal ends, a body graft material, and a plurality of body stents coupled to the body graft material, and wherein the mobile external coupling includes a coupling deployment device coupled thereto and to one of the plurality of body stents coupled to the body graft material, and wherein in the compressed configuration the mobile external coupling and coupling deployment device are in a collapsed configuration against the tubular body;

retracting an outer sleeve to expose the mobile external coupling such that the mobile external coupling is extended away from the tubular body to an extended configuration due to stored energy in the coupling deployment device;

aligning the mobile external coupling with the branch vessel; and deploying the tubular body such that the tubular body expands from the compressed configuration to an expanded configuration, wherein the tubular body is disposed in the main vessel and the mobile external coupling extends into the branch vessel, wherein the mobile external coupling extends outwardly from the tubular body, and wherein in the extended configuration the mobile external coupling includes a coupling graft material, a coupling lumen in flow communication with the body lumen, and wherein in the extended configuration the coupling deployment device is a continuous wire including a first base segment coupled to one of the plurality of body stents and extending generally transverse to a longitudinal axis of the mobile external coupling, a first spring arm coupled to the base segment and extending generally longitudinally relative to the mobile external coupling, and an apical segment having a first end coupled to the first spring arm and extending around at least a portion of the top of the mobile external coupling in a circumferential manner.

32. The method of claim 31, further comprising the steps of:

delivering a branch vessel prosthesis in a compressed configuration to the branch vessel; and deploying the branch vessel prosthesis such that the branch vessel prosthesis radially expands to an expanded configuration and an outside surface of a portion of the branch vessel prosthesis is in contact with an inner surface of a portion of the mobile external coupling.

33. The method of claim 31, wherein main vessel is the aortic arch.

34. The method of claim 31, wherein the apical segment is generally semicircular and wherein the coupling deployment device further includes a second spring arm coupled to a second end of the apical segment and extending generally longitudinally relative to the mobile external coupling, and a second base segment coupled to the second spring arm and to the body stent.

35. The method of claim 31, wherein the stored energy in the coupling deployment device provides an extension force between 80 and 120 grams-force when the mobile external coupling is exposed due to the step of retracting the first sleeve.

* * * * *